(12) United States Patent
Chai et al.

(10) Patent No.: US 10,926,438 B2
(45) Date of Patent: Feb. 23, 2021

(54) PRODUCTION METHOD OF MOLD HAVING RECESSED PEDESTAL PATTERN, AND MANUFACTURING METHOD OF PATTERN SHEET

(71) Applicant: FUJIFILM Corporation, Tokyo (JP)

(72) Inventors: Satoshi Chai, Kanagawa (JP); Toshihiro Usa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 17/026,286

(22) Filed: Sep. 20, 2020

(65) Prior Publication Data
US 2021/0001516 A1   Jan. 7, 2021

Related U.S. Application Data

(63) Continuation of application No. PCT/JP2019/012122, filed on Mar. 22, 2019.

(30) Foreign Application Priority Data

Mar. 27, 2018   (JP) .............................. JP2018-060598

(51) Int. Cl.
*B29C 45/14* (2006.01)
*A61M 37/00* (2006.01)
(Continued)

(52) U.S. Cl.
CPC ...... *B29C 45/1418* (2013.01); *B29C 33/3842* (2013.01); *B29C 39/02* (2013.01);
(Continued)

(58) Field of Classification Search
CPC ...... B29C 45/1418; B29C 2045/14213; B29C 2045/0094; B29C 45/263; B29C 45/2632;
(Continued)

(56) References Cited

U.S. PATENT DOCUMENTS

| | | | | | |
|---|---|---|---|---|---|
| 4,360,329 | A | * | 11/1982 | Hatakeyama | ....... B29C 45/1418 264/132 |
| 5,000,903 | A | * | 3/1991 | Matzinger | ........... B29C 45/1418 264/511 |

(Continued)

FOREIGN PATENT DOCUMENTS

| | | |
|---|---|---|
| JP | 2006096002 | 4/2006 |
| JP | 2015231476 | 12/2015 |

(Continued)

OTHER PUBLICATIONS

"International Search Report (Form PCT/ISA/210) of PCT/JP2019/012122," dated Jun. 18, 2019, with English translation thereof, pp. 1-4.

(Continued)

*Primary Examiner* — Benjamin A Schiffman
(74) *Attorney, Agent, or Firm* — JCIPRNET

(57) ABSTRACT

Provided are a production method of a mold having a recessed pedestal pattern for preventing a liquid flow and a manufacturing method of a pattern sheet. A production method of a mold having a recessed pedestal pattern, has: a step of preparing an insert mold having a protruding needle pattern group; a step of preparing a mold having a first mold provided with a protruding pedestal shape and a second mold; a holding step of holding the protruding pedestal shape of the first mold and the protruding needle pattern group of the insert mold in an overlapping manner; a clamping step of performing clamping with the first mold and the second mold to form a cavity; and an injection step of filling the cavity with a resin.

11 Claims, 24 Drawing Sheets

(51) Int. Cl.
  *B29C 33/38*    (2006.01)
  *B29C 39/02*    (2006.01)
  *C25D 1/10*     (2006.01)
  *B29C 59/02*    (2006.01)
  *B29C 45/26*    (2006.01)
  *B29K 101/10*   (2006.01)
  *B29K 83/00*    (2006.01)
  *B29L 31/00*    (2006.01)
  *B29C 45/00*    (2006.01)

(52) U.S. Cl.
  CPC ............ *B29C 45/263* (2013.01); *B29C 59/02* (2013.01); *C25D 1/10* (2013.01); *A61M 2037/0053* (2013.01); *B29C 2045/0094* (2013.01); *B29C 2045/14213* (2013.01); *B29C 2045/264* (2013.01); *B29C 2045/2697* (2013.01); *B29K 2083/00* (2013.01); *B29K 2101/10* (2013.01); *B29L 2031/756* (2013.01); *B29L 2031/759* (2013.01); *B29L 2031/7544* (2013.01)

(58) Field of Classification Search
  CPC ...... B29C 2045/2634; B29C 2045/264; B29C 2045/2697; C25D 1/10; A61M 2037/0053; B29L 2031/7544; B29L 2031/756; B29L 2031/759
  See application file for complete search history.

(56) References Cited

U.S. PATENT DOCUMENTS

| | | | | |
|---|---|---|---|---|
| 6,207,089 | B1* | 3/2001 | Chuang | B21D 26/055 264/135 |
| 7,641,845 | B2* | 1/2010 | Chang | B29C 45/1418 264/511 |
| 8,088,321 | B2* | 1/2012 | Ferguson | A61M 37/0015 264/328.7 |
| 8,236,231 | B2* | 8/2012 | Ferguson | A61M 37/0015 264/403 |
| 9,289,925 | B2* | 3/2016 | Ferguson | B29C 45/37 |
| 9,339,956 | B2* | 5/2016 | Rendon | A61M 37/0015 |
| 10,195,768 | B2* | 2/2019 | Ogawa | B29C 39/36 |
| 10,300,261 | B2* | 5/2019 | Shiomitsu | B81C 1/00 |
| 10,465,798 | B2* | 11/2019 | Saso | F16J 15/102 |
| 10,648,095 | B2* | 5/2020 | Chai | B29C 33/424 |
| 10,814,527 | B2* | 10/2020 | Ogawa | A61M 37/0015 |
| 2007/0102110 | A1* | 5/2007 | Yuba | B32B 3/28 156/285 |
| 2007/0191761 | A1* | 8/2007 | Boone | B29C 33/3842 604/46 |
| 2008/0144324 | A1 | 6/2008 | Tahara et al. | |
| 2008/0275400 | A1* | 11/2008 | Ferguson | B29C 45/561 604/173 |
| 2009/0194908 | A1* | 8/2009 | Chen | B29C 45/37 264/328.1 |
| 2017/0095946 | A1* | 4/2017 | Ogawa | B29C 33/38 |
| 2018/0215078 | A1* | 8/2018 | Ogawa | B29C 41/20 |
| 2018/0222088 | A1* | 8/2018 | Ogawa | B29C 33/424 |
| 2018/0250851 | A1* | 9/2018 | Ogawa | B29C 39/02 |
| 2018/0311877 | A1* | 11/2018 | Saifullah | B29C 45/37 |
| 2019/0001540 | A1* | 1/2019 | Yui | F16J 15/10 |
| 2019/0070754 | A1 | 3/2019 | Ogawa et al. | |
| 2019/0351588 | A1* | 11/2019 | Sakazaki | B29C 39/26 |
| 2020/0094034 | A1* | 3/2020 | Okano | B29C 41/12 |
| 2020/0282604 | A1* | 9/2020 | Mochizuki | B29C 33/40 |

FOREIGN PATENT DOCUMENTS

| | | |
|---|---|---|
| JP | 2017202040 | 11/2017 |
| JP | 2017209155 | 11/2017 |
| WO | 2006098137 | 9/2006 |

OTHER PUBLICATIONS

"Written Opinion of the International Searching Authority (Form PCT/ISA/237) of PCT/JP2019/012122," dated Jun. 18, 2019, with English translation thereof, pp. 1-8.

* cited by examiner

FIG. 10
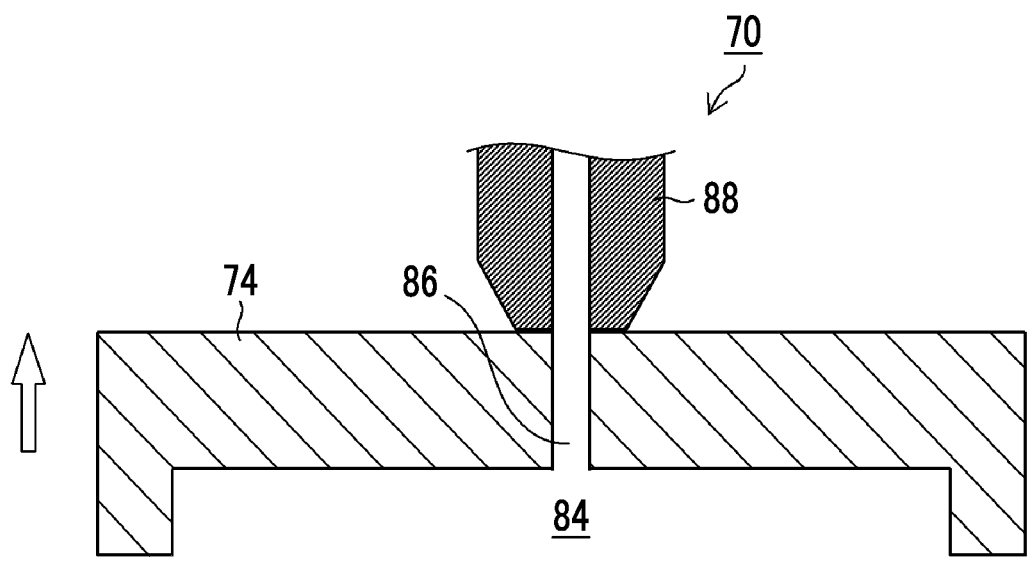
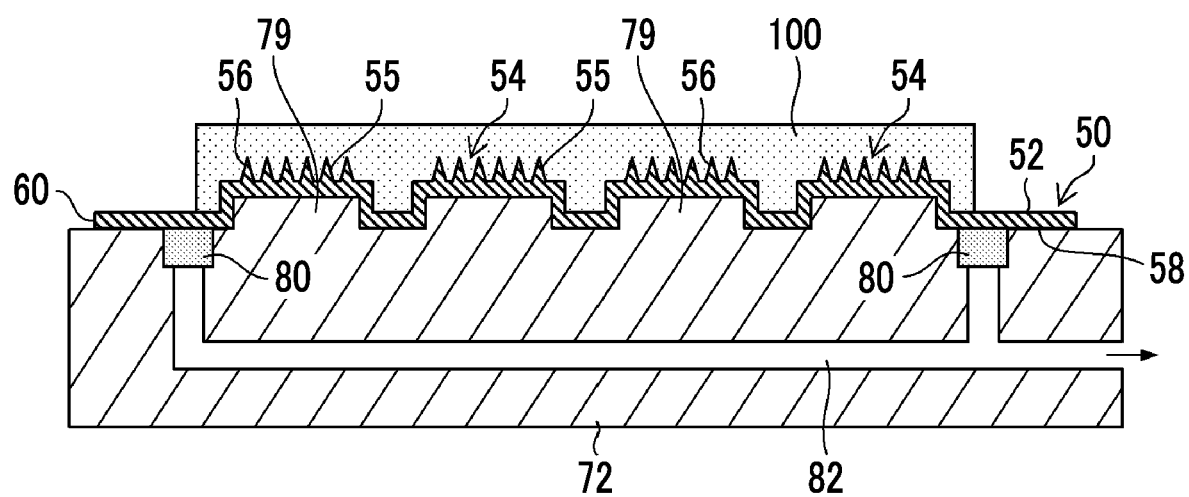

FIG. 13
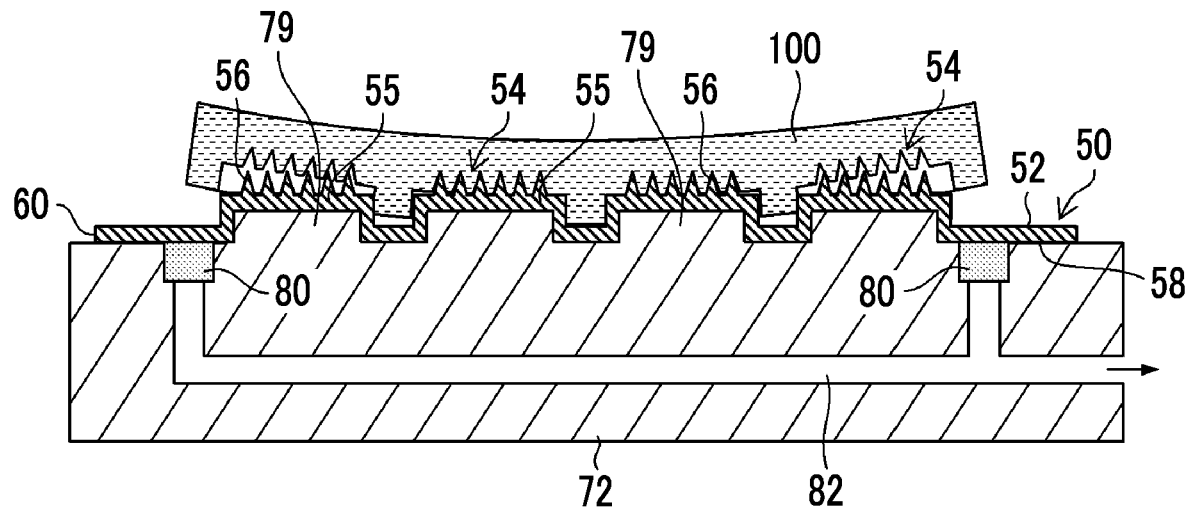
FIG. 14
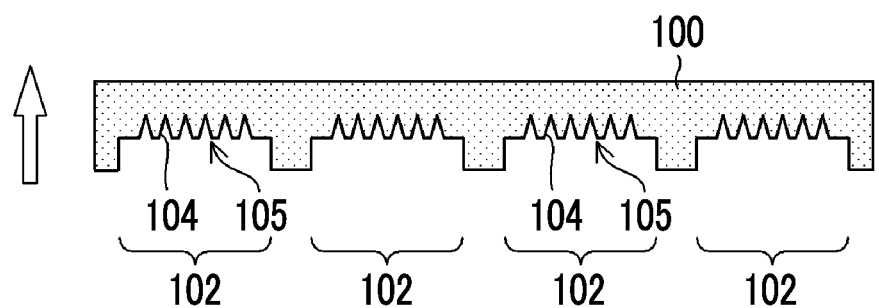
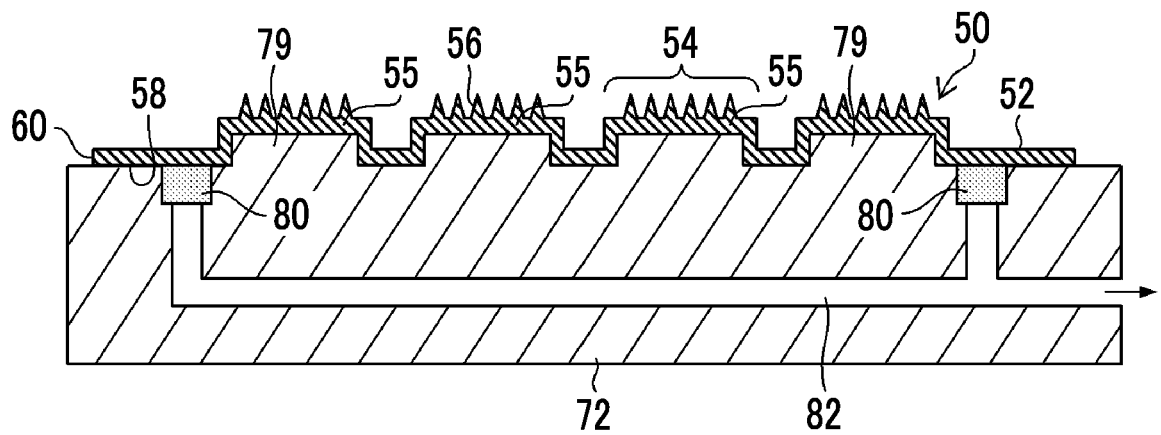

FIG. 15
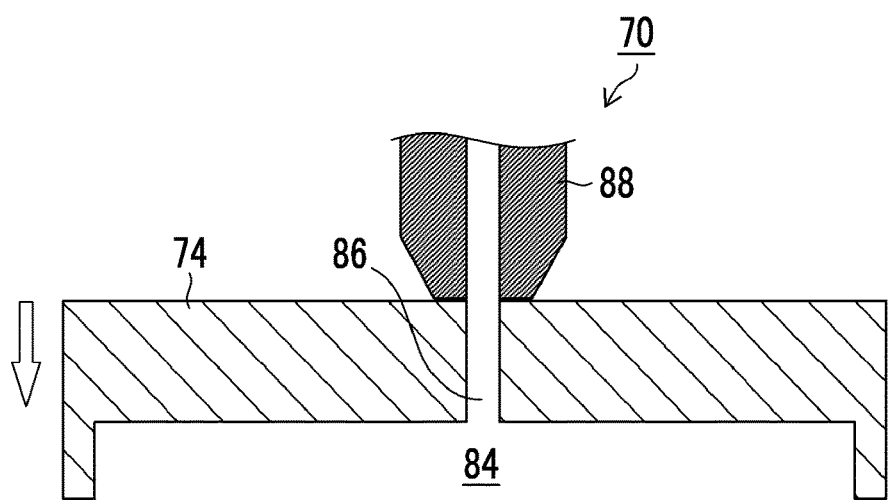
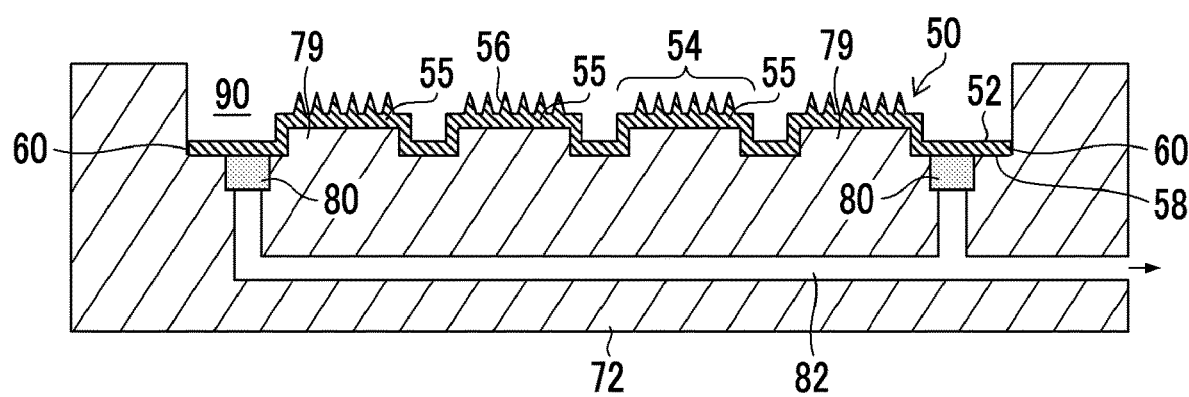

PRODUCTION METHOD OF MOLD HAVING RECESSED PEDESTAL PATTERN, AND MANUFACTURING METHOD OF PATTERN SHEET

CROSS-REFERENCE TO RELATED APPLICATIONS

The present application is a Continuation of PCT International Application No. PCT/JP2019/012122 filed on Mar. 22, 2019 claiming priority under 35 U.S.C. § 119(a) to Japanese Patent Application No. 2018-060598 filed on Mar. 27, 2018. Each of the above applications is hereby expressly incorporated by reference, in its entirety, into the present application.

BACKGROUND OF THE INVENTION

1. Field of the Invention

The present invention relates to a production method of a mold having a recessed pedestal pattern and a manufacturing method of a pattern sheet, and particularly to a production method of a mold having a recessed pedestal pattern used for manufacturing a pattern sheet having needle-like protrusions, and a manufacturing method of a pattern sheet using the mold having the recessed pedestal pattern.

2. Description of the Related Art

In recent years, as a novel dosage form capable of injecting drugs such as insulin, vaccines, and human growth hormone (hGH) into the skin without pain, a microneedle array has been known. The microneedle array is an array of microneedles (also referred to as needle-like protrusions, fine needles, or small needles) which contain drugs and are biodegradable. By attaching this microneedle array to the skin, each microneedle pierces the skin, and these microneedles are absorbed in the skin such that the drugs contained in each microneedle can be administered into the skin. Microneedle arrays are also called percutaneous absorption sheets.

In order to produce a molded product having a fine pattern such as a microneedle array, a resin mold having an inverted shape is formed from a plate precursor having the fine pattern, and a molded product is produced from the mold. There is a demand for improving the productivity of molded products having such fine patterns, and various proposals have been made.

For example, JP2017-209155A and JP2017-202040A describe a technique of producing a mold by injection molding in which an electroform is clamped between a first mold and a second mold and the cavity therebetween is filled with a resin. According to JP2017-209155A and JP2017-202040A, an accurate mold can be produced.

On the other hand, in JP2015-231476A describes a mold which is provided with a step in order to prevent a resin solution forming a pattern sheet from flowing out of the mold and flowing beyond a target location when the pattern sheet is formed. By using the mold having the step, it is possible to prevent a liquid containing no drug from flowing out of the mold when the liquid containing no drug is applied to the surface of the mold.

SUMMARY OF THE INVENTION

However, JP2015-231476A does not disclose a configuration in which a mold having a configuration for preventing a liquid flow is produced by injection molding.

The present invention has been made taking the above circumstances into consideration, and an object thereof is to provide a production method of a mold having a recessed pedestal pattern for preventing a liquid flow, and a manufacturing method of a pattern sheet.

In order to achieve the object, a production method of a mold having a recessed pedestal pattern according to an aspect comprises: a step of preparing an insert mold having a protruding needle pattern group; a step of preparing a mold having a first mold provided with a protruding pedestal shape and a second mold; a holding step of holding the protruding pedestal shape of the first mold and the protruding needle pattern group of the insert mold in an overlapping manner; a clamping step of performing clamping with the first mold and the second mold to form a cavity; and an injection step of filling the cavity with a resin.

According to the aspect, since the protruding pedestal shape of the first mold and the protruding needle pattern group of the insert mold are held in an overlapping manner, it is possible to produce a mold having a recessed pedestal pattern that prevents a liquid from flowing to a position of an inverted pattern of the protruding needle pattern group.

It is preferable that the insert mold has the protruding needle pattern group on a front surface of a protruding pedestal shape having a recess on a rear surface, and in the holding step, the protruding pedestal shape of the first mold and the recess of the insert mold are held in an overlapping manner. Accordingly, the protruding pedestal shape of the first mold and the protruding needle pattern group of the insert mold can be appropriately held in an overlapping manner.

It is preferable that in the injection step, the insert mold is deformed following the protruding pedestal shape of the first mold to form a protruding pedestal shape having a recess on a rear surface of the insert mold. Accordingly, the recessed pedestal pattern can be appropriately produced.

It is preferable that the insert mold has the same size as the protruding pedestal shape in a plan view or is smaller than the protruding pedestal shape. Accordingly, the recessed pedestal pattern can be appropriately produced.

It is preferable that the resin is any one of a thermosetting resin and a silicone resin. Accordingly, the mold can be appropriately produced.

It is preferable that after the injection step, a curing step of heating the resin in the cavity to cure the resin, and after the curing step, a releasing step of opening the first mold and the second mold and releasing the cured resin from the insert mold are included. Accordingly, the mold can be appropriately produced.

It is preferable that the insert mold is made of any one of a plastic resin and a metal. Accordingly, the mold can be appropriately produced.

It is preferable that the insert mold is an electroform and is circular in a plan view. Accordingly, the insert mold can be appropriately produced.

It is preferable that in the clamping step, the insert mold is clamped by the first mold and the second mold. Accordingly, the cavity can be appropriately formed.

In order to achieve the object, a production method of a mold having a recessed pedestal pattern according to an aspect comprises: a step of producing a first mold having a recessed pedestal pattern by the production method of a mold having a recessed pedestal pattern; an electroforming step of forming a metal body on the recessed pedestal pattern of the first mold by an electroforming treatment; a peeling step of peeling the metal body that is an electroform from the first mold; and a step of producing a second mold by the production method of a mold having a recessed pedestal pattern, using the electroform as the insert mold.

According to the aspect, since the electroform is produced from the first mold having the recessed pedestal pattern, and the second mold having the recessed pedestal pattern is produced from the electroform, it is possible to produce a plurality of molds from a single mold.

In order to achieve the object, a manufacturing method of a pattern sheet according to an aspect, comprises: a step of producing a mold having a recessed pedestal pattern by the production method of a mold having a recessed pedestal pattern; a supplying step of supplying a polymer solution to the recessed pedestal pattern of the mold; a drying step of drying the polymer solution to form a polymer sheet; and a polymer sheet releasing step of releasing the polymer sheet from the mold.

According to the aspect, since the polymer solution does not overflow from the recessed pedestal pattern, the pattern sheet can be appropriately manufactured.

It is preferable that the polymer solution contains a water-soluble material. This aspect can be applied to a polymer solution containing a water-soluble material.

According to the present invention, a mold configured to prevent a liquid flow can be produced by injection molding. In addition, a pattern sheet can be manufactured using the mold.

BRIEF DESCRIPTION OF THE DRAWINGS

FIG. 10 is a process diagram illustrating the production method of a mold.

FIG. 13 is a process diagram illustrating the production method of a mold.

FIG. 14 is a process diagram illustrating the production method of a mold.

FIG. 15 is a process diagram illustrating a production method of another mold.

DESCRIPTION OF THE PREFERRED EMBODIMENTS

Figure 1:
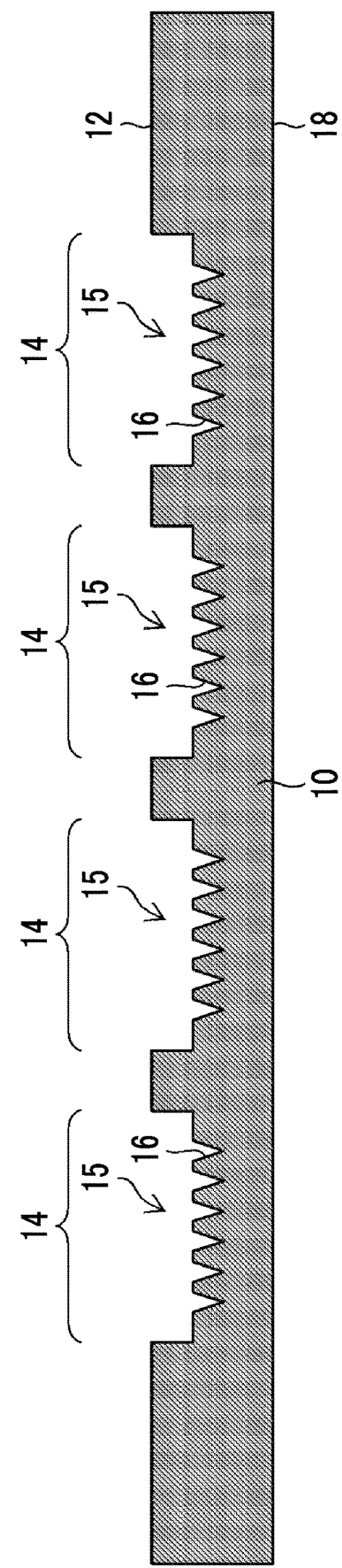
FIG. 1 is a process diagram illustrating a production method of an electroform.

Hereinafter, preferred embodiments of the present invention will be described with reference to the accompanying drawings. The present invention is described by the following preferred embodiments. Modifications can be made by various methods without departing from the scope of the present invention, and other embodiments than the present embodiment can also be used. Therefore, all modifications within the scope of the present invention are included in the appended claims.

Here, in the figures, like elements having similar functions are denoted by like reference numerals. In addition, in this specification, in a case where a numerical value range is expressed using "to", the numerical value range includes the numerical values of the upper limit and the lower limit indicated by "to".

First Embodiment

<Production Method of Mold>

An embodiment of the present invention will be described with reference to the drawings. A production method of a mold having a recessed pedestal pattern of the present embodiment, comprises: a step of preparing an insert mold having a protruding needle pattern group; a step of preparing a mold having a first mold provided with a protruding pedestal shape and a second mold; a holding step of holding the protruding pedestal shape of the first mold and the protruding needle pattern group of the insert mold in an overlapping manner; a clamping step of performing clamping with the first mold and the second mold to form a cavity; and an injection step of filling the cavity with a resin.

The insert mold used for the production of the mold is prepared. For example, the insert mold is produced based on process diagrams illustrated in FIGS. 1 to 4. As illustrated in FIG. 1, a master model 10 for producing an electroform which is the insert mold is prepared. On a first surface 12 of the master model 10, a recessed pattern 14 which is an inverted shape of the electroform having a protruding pattern to be produced is formed. The recessed pattern 14 is a state in which a plurality of second recesses 16 are arranged in a first recess 15 in an array. The first recesses 15 and the second recesses 16 are produced according to the shape of the electroform to be produced. In the present embodiment, the first recess 15 has a cylindrical shape having a constant diameter from the first surface 12 toward a second surface 18. In addition, the second recess 16 has a shape tapered from the first surface 12 toward the second surface 18. Example of the tapered shape may include a cone shape, a combination of a column shape and a cone shape, and a combination of a frustum shape and a cone shape. In the present embodiment, a plurality of the recessed patterns 14 are formed on the first surface 12 of the master model 10.

Figure 2:
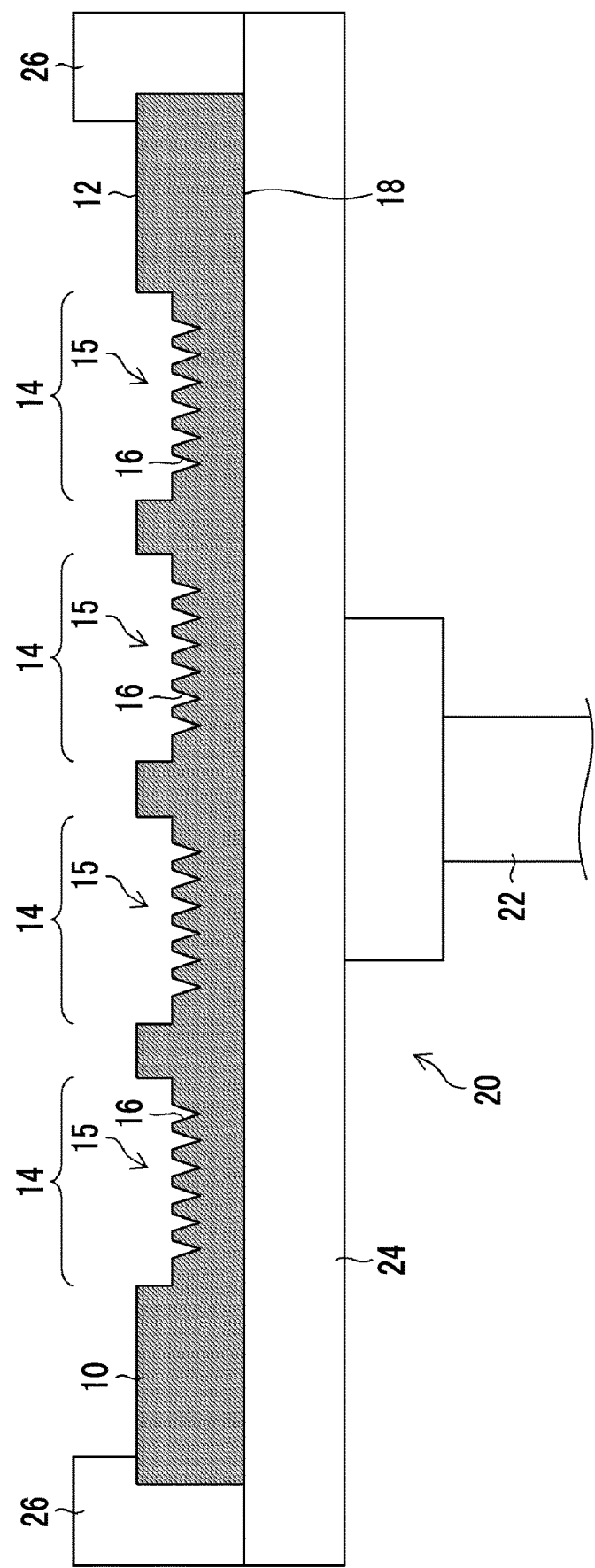
FIG. 2 is a process diagram illustrating the production method of an electroform.

As illustrated in FIG. 2, the master model 10 is fixed to a cathode 20 used in an electroforming treatment. The cathode 20 comprises at least a shaft 22 and a cathode plate 24. The master model 10 is fixed to the cathode plate 24 at a position where the second surface 18 of the master model 10 and the cathode plate 24 face each other.

In a case where the master model 10 is made of a resin material, a conduction treatment is performed on the master model 10. A metal film (for example, nickel) is formed on the first surface 12 and the recessed patterns 14 of the master model 10 by vapor deposition, sputtering, or the like. In order to supply a current from the cathode plate 24 to the metal film (not illustrated), a conductive ring 26 is provided at the outer peripheral portion of the master model 10. The shaft 22 and the cathode plate 24 are formed of a conductive member. Here, the electroforming treatment refers to a treatment method of depositing metal on the surface of the master model 10 by an electroplating method.

Figure 3:
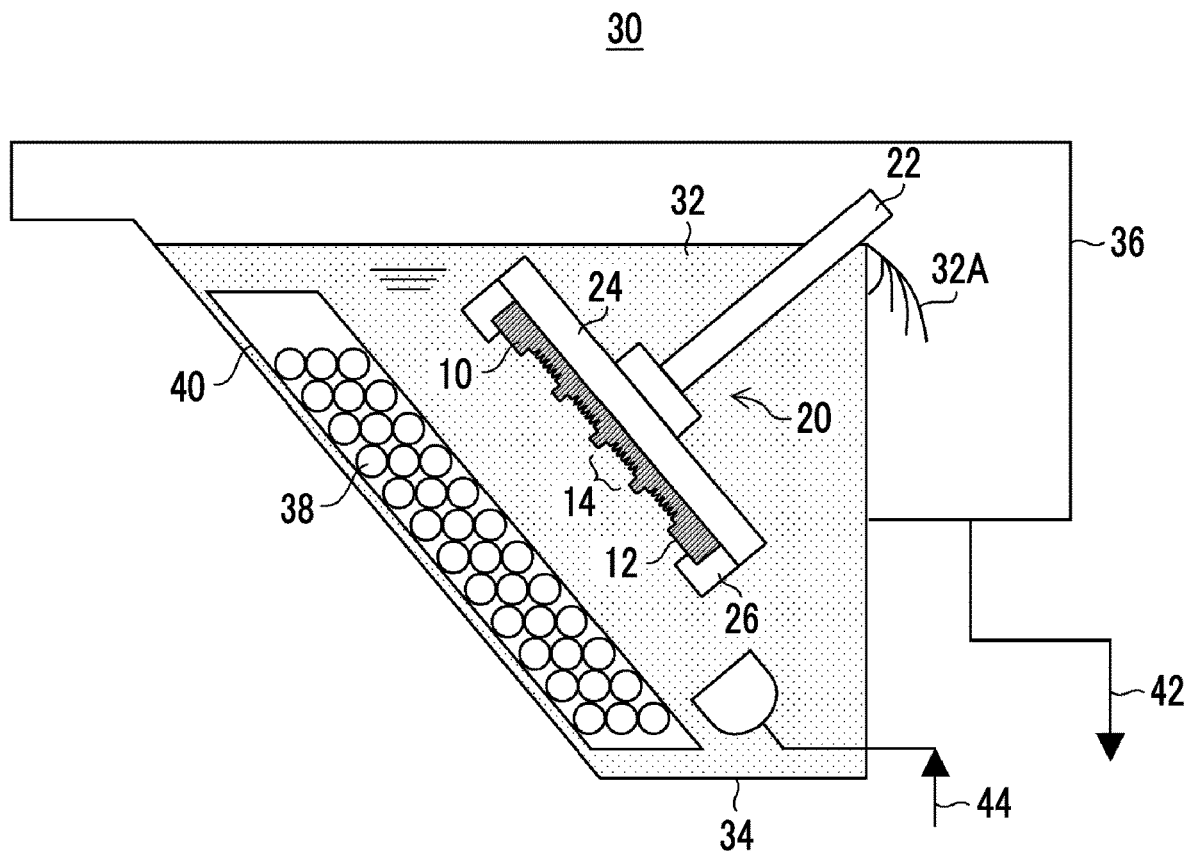
FIG. 3 is a process diagram illustrating the production method of an electroform.

As illustrated in FIG. 3, the master model 10 attached to the cathode 20 is immersed in an electroforming liquid 32. As illustrated in FIG. 3, an electroforming apparatus 30 for performing the electroforming treatment on the master model 10 comprises an electroforming tank 34 that holds the electroforming liquid 32, a drain tank 36 that receives an electroforming liquid 32A overflowing from the electroforming tank 34, and a titanium case 40 filled with Ni pellets 38. By immersing the cathode 20 having the master model 10 attached thereto in the electroforming liquid 32, the electroforming apparatus 30 operates. As the electroforming liquid 32, for example, a liquid in which 400 to 800 g/L of nickel sulfamate, 20 to 50 g/L of boric acid, and necessary additives such as a surfactant (for example, sodium lauryl sulfate) are mixed can be used. The temperature of the electroforming liquid 32 is preferably 40° C. to 60° C.

A drain pipe 42 is connected to the drain tank 36, and a supply pipe 44 is connected to the electroforming tank 34. The electroforming liquid 32 overflowing from the electroforming tank 34 to the drain tank 36 is recovered by the drain pipe 42, and the recovered electroforming liquid 32 is supplied from the supply pipe 44 to the electroforming tank 34. The master model 10 held by the cathode 20 is located at a position at which the first surface 12 on which the recessed patterns 14 are formed faces the titanium case 40 serving as an anode.

The cathode 20 is connected to a negative electrode, and a positive electrode is connected to the titanium case 40 serving as the anode. A direct current voltage is applied between the cathode 20 and the titanium case 40 while the master model 10 held by the cathode plate 24 is rotated about the shaft 22 at a rotational speed of 10 to 150 rpm. The Ni pellets 38 are melted such that a metal film adheres to the recessed patterns 14 of the master model 10 attached to the cathode 20.

Figure 4:
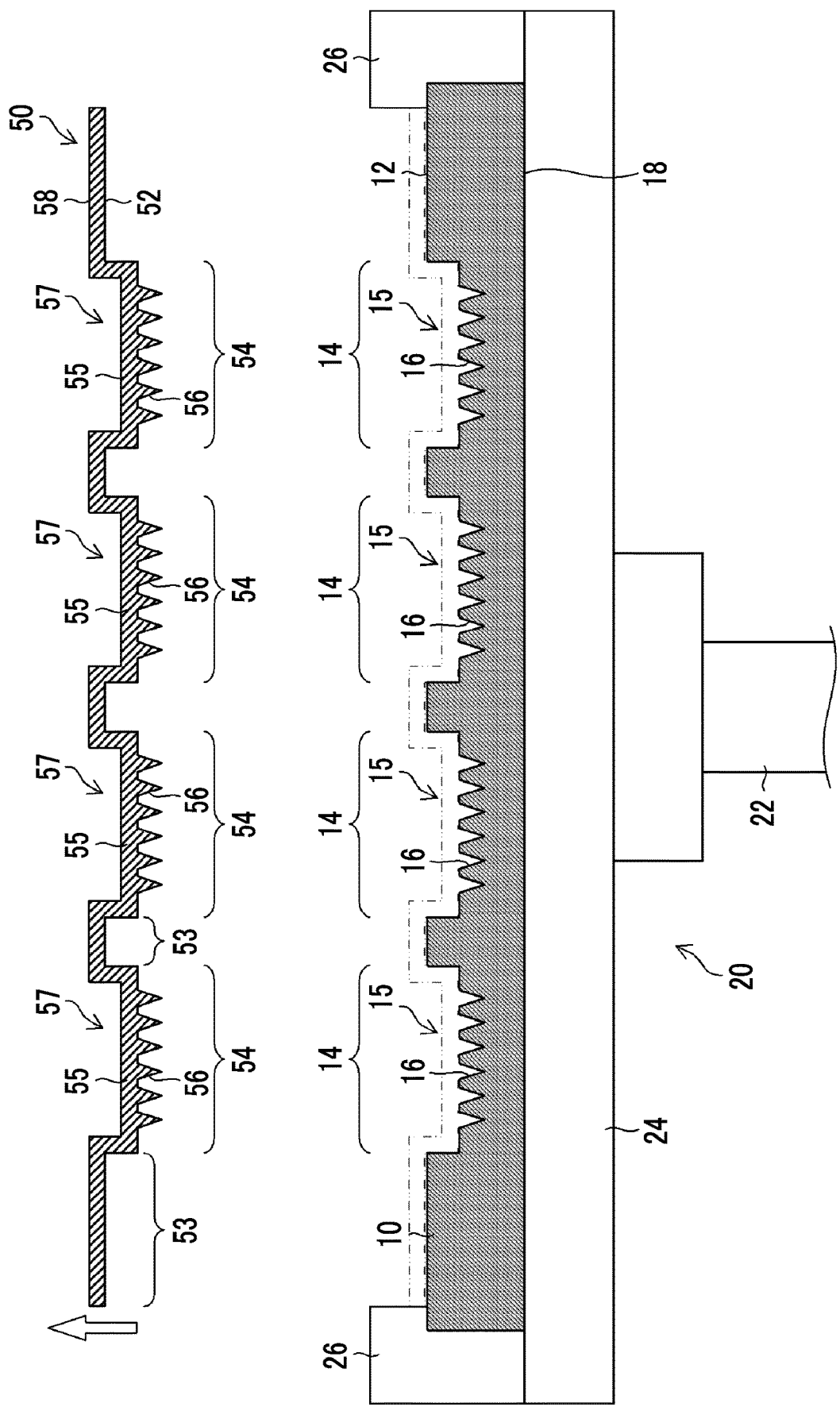
FIG. 4 is a process diagram illustrating the production method of an electroform.

As an electroform 50 made of the metal film is formed on the master model 10, as illustrated in FIG. 4, the cathode 20 to which the master model 10 is attached is taken out from the electroforming tank 34 (not illustrated). Next, the electroform 50 is peeled off from the master model 10. The electroform 50 having a first surface 52 and a second surface 58 and having flat portions 53 and protruding patterns 54 on the first surface 52 can be obtained. The protruding pattern 54 has an inverted shape of the recessed pattern 14 of the master model 10. Here, the electroform 50 has a thickness of 150 μm.

Figure 5:
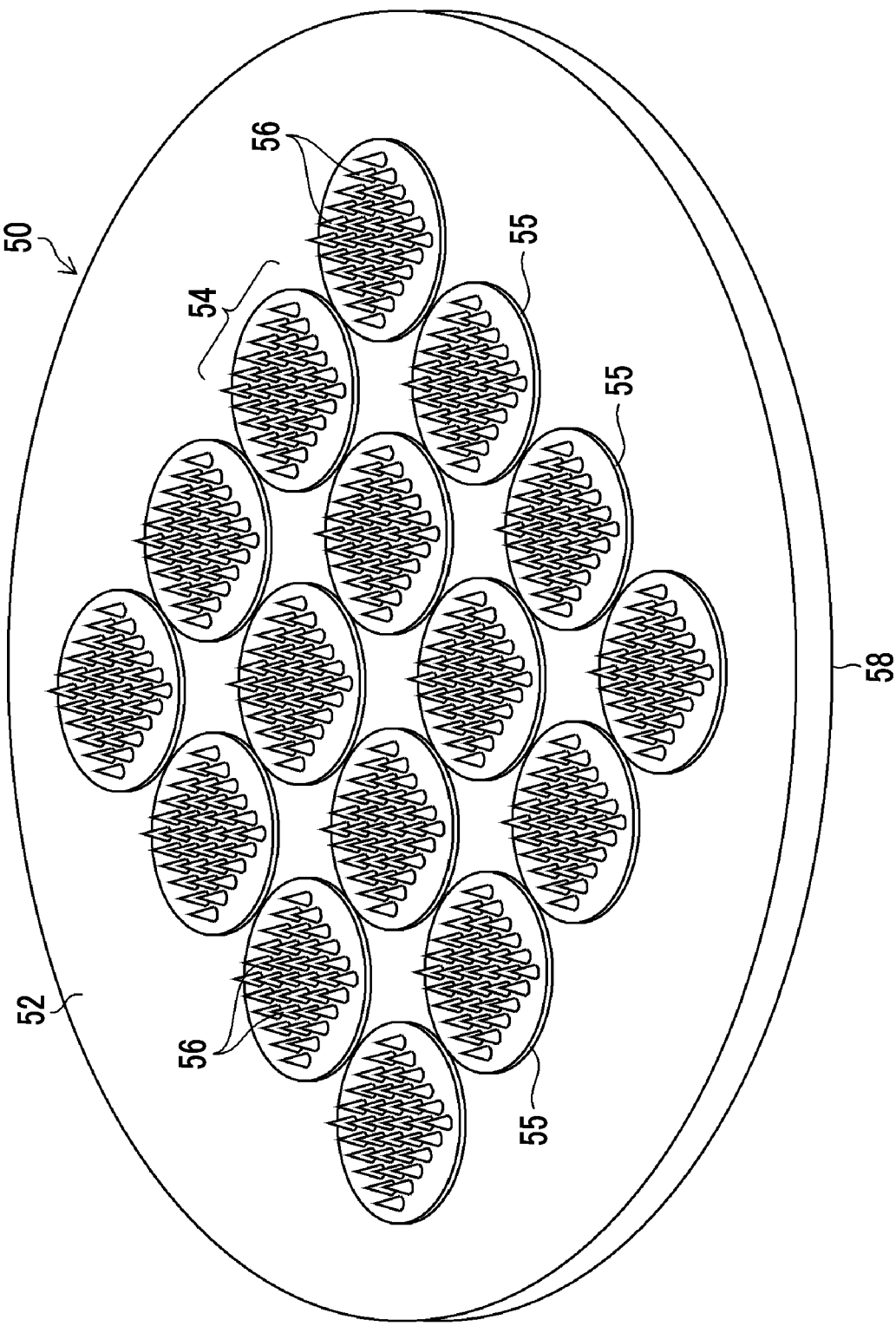
FIG. 5 is a perspective view of the electroform.

FIG. 5 is a perspective view of the electroform 50. As illustrated in FIG. 5, the protruding pattern 54 is a state in which a plurality of second protrusions 56, which are a protruding needle pattern group, are arranged in an array on a first protrusion 55, which is a protruding pedestal shape. In the present embodiment, the first protrusion 55 has a cylindrical pedestal shape having a constant height. The height of the first protrusion 55 is, for example, in a range of 0.2 mm or more and 2 mm or less, and preferably 0.3 mm or more and 1.5 mm or less. On the rear surface side of the first protrusion 55, a cylindrical recess 57 having a constant diameter is provided.

The second protrusion 56 has a tapered shape protruding from the first surface 52 of the first protrusion 55. Example of the tapered shape may include a cone shape, a combination of a column shape and a cone shape, and a combination of a frustum shape and a cone shape. In the present embodiment, a plurality of the protruding patterns 54 are formed on the first surface 52 of the electroform 50. The height of the second protrusion 56 is, for example, in a range of 0.2 mm or more and 2 mm or less, and preferably 0.3 mm or more and 1.5 mm or less. The height of the second protrusion 56 is the distance from the first protrusion 55 to the tip of the second protrusion 56.

In the electroforming treatment, in order to form a metal film of a uniform thickness on the first surface 12 of the master model 10, the electroform 50 preferably has a circular shape in a plan view. The diameter of the electroform 50 is preferably 200 to 300 mm. The circular shape is not limited to a perfect circle and may be a substantially circular shape.

Although the electroform 50 made of metal is produced as the insert mold here, the insert mold may be made of a plastic resin. The thickness of the insert mold is not limited.

As will be described later, by performing injection molding using the electroform 50, the electroform 50 is transferred and a mold is produced. As illustrated in FIG. 5, the area of a region in which the plurality of protruding patterns 54 are formed is smaller than the area of the electroform 50. In a case where a mold is produced on the entire surface of the electroform 50, the produced mold may exceed an appropriate size and may include a surplus portion. This surplus portion causes a loss of the resin and may require additional work such as cutting.

In the injection molding, in order to easily fix and replace the electroform 50, the electroform 50 may be vacuum-adsorbed using an adsorption plate. It is required that the adsorption plate is not damaged during the injection molding.

A production method of a mold by injection molding will be described with reference to process diagrams of FIGS. 6 to 16.

Figure 6:
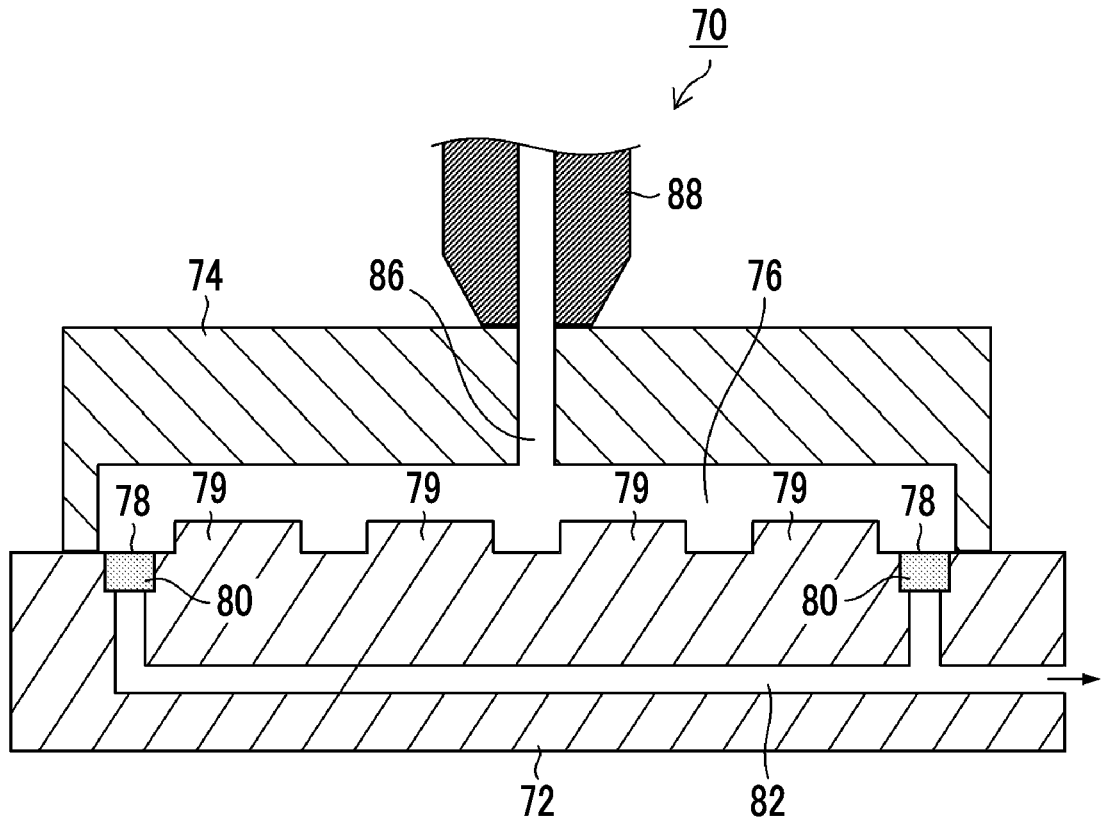
FIG. 6 is a process diagram illustrating a production method of a mold.

As illustrated in FIG. 6, a mold 70 including a first mold 72 and a second mold 74 is prepared. By clamping the first mold 72 and the second mold 74, a cavity 76 is formed inside the mold 70. The cavity 76 means a space filled with a resin.

The electroform 50 is fixed to the first mold 72. The side to which the electroform 50 is fixed is formed of a flat surface 78 and a pedestal support portion 79. The pedestal support portion 79 has a cylindrical pedestal shape having a constant height. The height of the pedestal support portion 79 and the depth of the recess 57 on the rear surface side of the first protrusion 55 of the electroform 50 are substantially equal. The diameter of the pedestal support portion 79 and the diameter of the recess 57 are substantially equal.

Here, an example in which the recess 57 has a cylindrical shape and the pedestal support portion 79 has a cylindrical shape has been described. However, in a case where the recess 57 has a rectangular tube shape, the pedestal support portion 79 is caused to have a rectangular column shape.

The first mold 72 comprises an adsorption plate 80 on the flat surface 78 as a device for fixing the electroform 50. The first mold 72 comprises a suction pipe 82 in which gas communicates with the adsorption plate 80. The suction pipe 82 is connected to a vacuum pump (not illustrated). By driving the vacuum pump, air can be suctioned from the surface of the adsorption plate 80. By using the adsorption plate 80, the electroform 50 can be easily fixed and replaced.

For example, the adsorption plate 80 is formed of a porous member. Examples of the porous member include a metal sintered body, a resin, and a ceramic. It is required that the adsorption plate 80 is not damaged from the viewpoint of strength.

In a case where the electroform 50 is formed of a ferromagnetic material such as nickel, the electroform 50 may be held by the first mold 72 by the magnetic force of a magnet (not illustrated) provided in the first mold 72.

A depression 84 (see FIG. 10) is formed on the cavity 76 side of the second mold 74. In the present embodiment, the cavity 76 is formed by the flat surface 78 of the first mold 72 and the depression 84 of the second mold 74. By configuring the first mold 72 and the second mold 74 as described above, releasing of the mold is facilitated as described later.

A gate 86 that communicates with the cavity 76 is formed in the second mold 74. The gate 86 serves as an injection port for a resin into the cavity 76 of the mold 70. The gate 86 communicates with an injection molding machine 88 that supplies the resin into the mold 70. In the present embodiment, the cavity 76 is filled with the resin in a direction substantially perpendicular to the longitudinal direction of the cavity 76, a so-called vertical direction (injection step).

Figure 7:
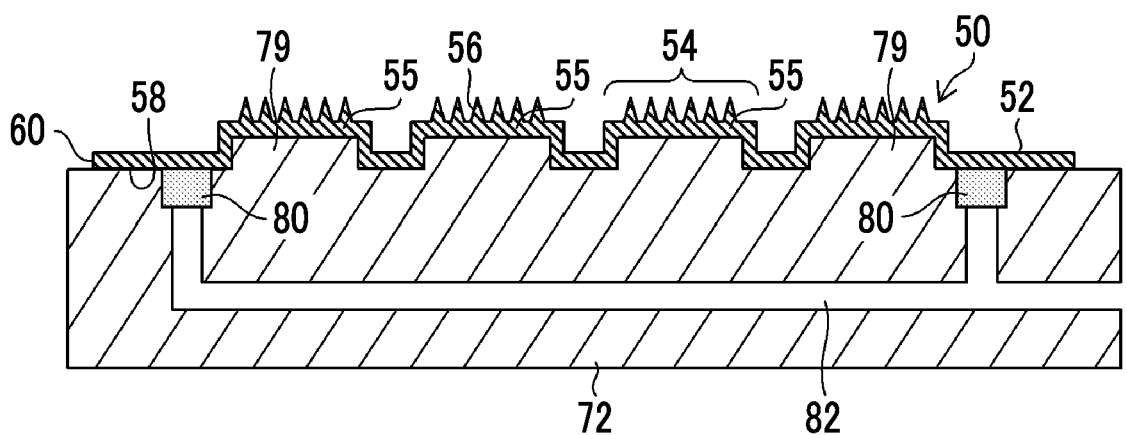
FIG. 7 is a process diagram illustrating the production method of a mold.

As illustrated in FIG. 7, the first mold 72 and the second mold 74 are opened, and the electroform 50 having the protruding patterns 54 is placed on the first mold 72. The pedestal support portion 79 of the first mold 72 fits into the recess 57 of the electroform 50. By suctioning air using the vacuum pump via the suction pipe 82, the second surface 58 of the electroform 50 is vacuum-adsorbed onto the adsorption plate 80. As described above, the pedestal support portion 79 of the first mold 72 and the protruding pattern 54 of the electroform 50 are held in an overlapping manner.

Figure 8:
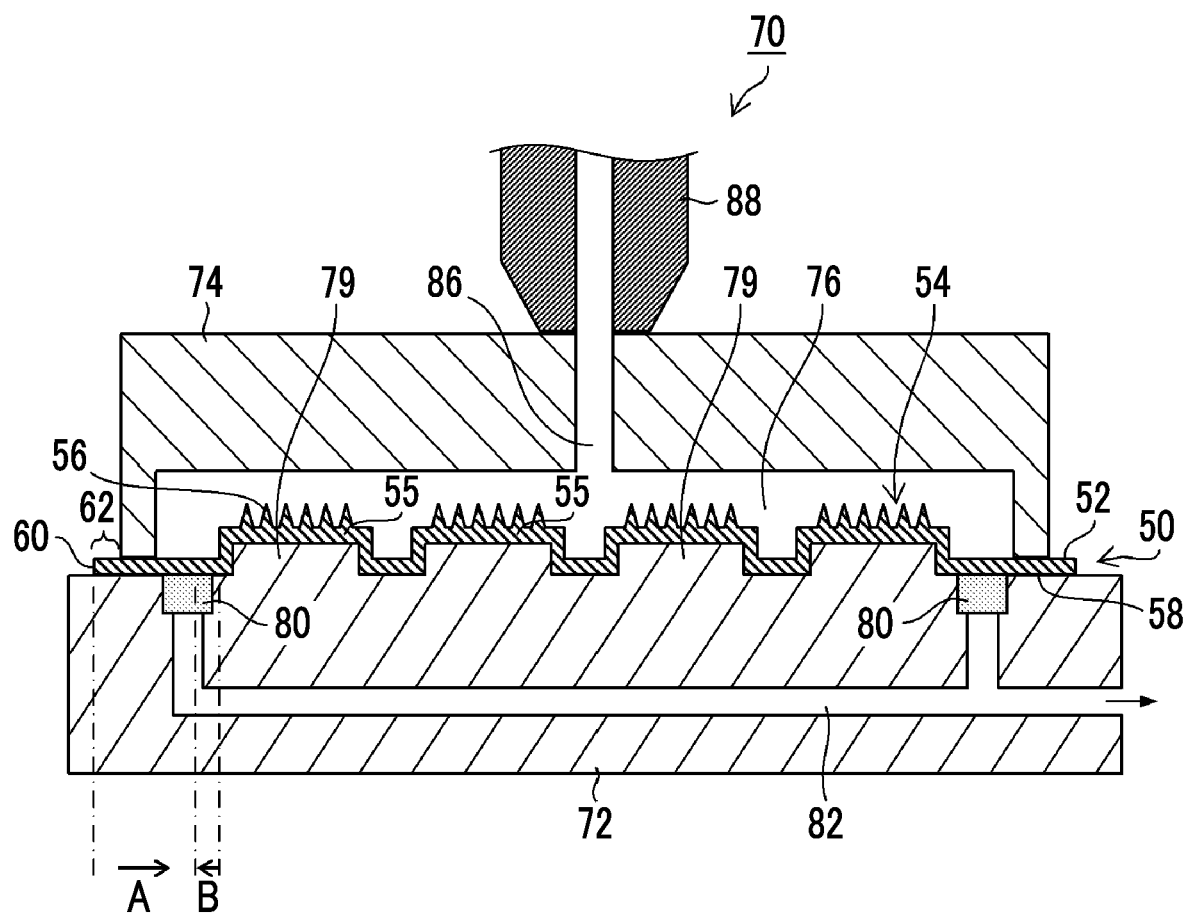
FIG. 8 is a process diagram illustrating the production method of a mold.

As illustrated in FIG. 8, in a clamping step, in order to form the cavity 76, the electroform 50 is clamped by the first mold 72 and the second mold 74 in a region other than the protruding patterns 54 of the electroform 50, and substantially in a region other than the adsorption plate 80.

Clamping of the electroform 50 by the first mold 72 and the second mold 74 substantially in the region other than the adsorption plate 80 means a case where the electroform 50 is clamped by the first mold 72 and the second mold 74 in a region other than the adsorption plate 80 and a case where the electroform 50 is clamped by the first mold 72 and the second mold 74 in a region including a portion of the adsorption plate 80, and means that the adsorption plate 80 is not damaged by the clamping.

Since the electroform 50 is clamped by the first mold 72 and the second mold 74, as indicated by arrow A in FIG. 8, the inner wall of the second mold 74 is located inward of an outer edge 60 of the electroform 50. In a plan view, the cavity 76 is smaller than the entire surface of the electroform 50, and as a result, the volume of the cavity 76 can be reduced, so that a loss of the resin can be avoided.

In the present embodiment, the first mold 72 and the second mold 74 do not clamp the electroform 50 in the region of the adsorption plate 80. As indicated by arrow B in FIG. 8, since the inner wall of the second mold 74 is located outside the adsorption plate 80, it is possible to avoid damage to the adsorption plate 80. Inward is a direction from the outer edge 60 of the electroform 50 toward the center, and outward is a direction from the center of the electroform 50 toward the outer edge 60. It is important to determine the position of the inner wall that defines the size of the cavity 76 (the inner wall that defines the width direction, not the height direction) so that the adsorption plate 80 is not damaged. As long as the adsorption plate 80 is not damaged, a region of a portion of the adsorption plate 80 can be clamped by the first mold 72 and the second mold 74.

In the present embodiment, a region of the electroform 50 excluding an end portion 62 is clamped. As illustrated in FIG. 4, the electroform 50 is produced by supplying a current from the conductive ring 26. Therefore, there may be cases where the end portion 62 of the electroform 50, which is in contact with the conductive ring 26, has different physical properties (for example, thickness and surface roughness) compared to the other portions of the electroform 50.

In a case where the electroform 50 has the end portion 62 having different physical properties, during injection molding using the electroform 50, there is concern about accuracy of a produced molded product due to unstable fixing of the electroform 50 by the first mold 72 and the second mold 74, and the like. Therefore, as in the present embodiment, the end portion 62 is preferably not clamped.

However, in a case where there is no problem in the accuracy of the produced molded product, the end portion 62 of the electroform 50 may be clamped by the first mold 72 and the second mold 74. The end portion 62 of the electroform 50 is a region inward of the outer edge of the electroform 50 and is a region having physical properties different from those of the other regions excluding the protruding patterns 54 of the electroform 50. In addition, the physical properties are not limited to thickness.

According to the present embodiment, without processing the end portion 62 of the electroform 50, the produced electroform 50 can be fixed to the inside of the mold 70, so that it is possible to realize injection molding with high productivity. In addition, since the electroform 50 is vacuum-adsorbed by the adsorption plate 80 and is clamped by the first mold 72 and the second mold, the electroform 50 can be stably fixed, so that it is possible to realize injection molding with high accuracy.

Figure 9:
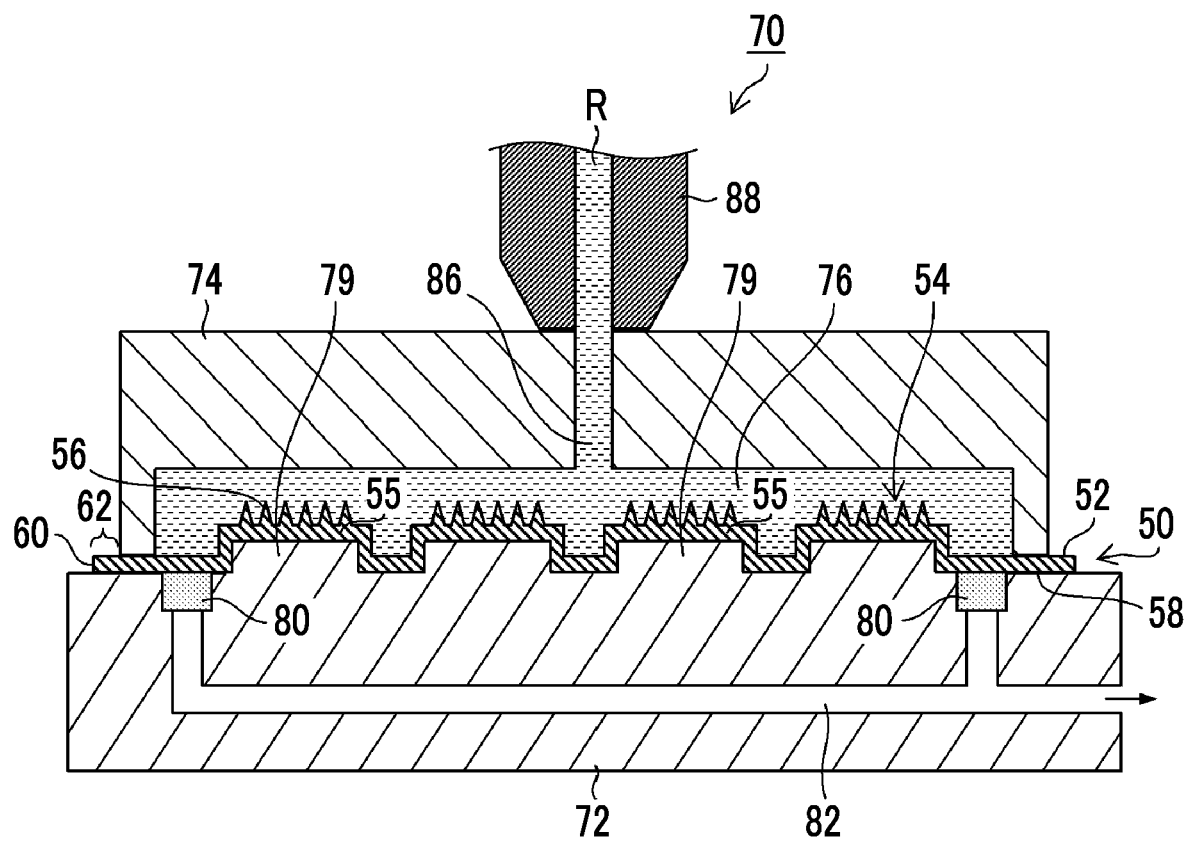
FIG. 9 is a process diagram illustrating the production method of a mold.

As illustrated in FIG. 9, a resin R is supplied from the injection molding machine 88 to the cavity 76 via the gate 86. The resin R fills the cavity 76 while passing through between the protruding patterns 54 of the electroform 50. As the resin R, a thermosetting resin such as an acrylic or epoxy resin or a silicone resin is preferably used, and particularly, a silicone resin is preferably used. In a case where the cavity 76 of the mold 70 is filled with the resin R, the resin R is then heated and the resin R is cured (curing step).

As illustrated in FIG. 10, in order to release the cured resin R from the electroform 50, the first mold 72 and the second mold 74 clamped are opened. During the opening, the first mold 72 and the second mold 74 are moved away from each other. As illustrated in FIG. 10, the second mold 74 has the depression 84 for forming the cavity 76. The cured resin R is a mold 100 on which recessed patterns 102 (see FIG. 14) before releasing are formed. Hereinafter, the cured resin R is sometimes referred to as the mold 100.

Figure 11:
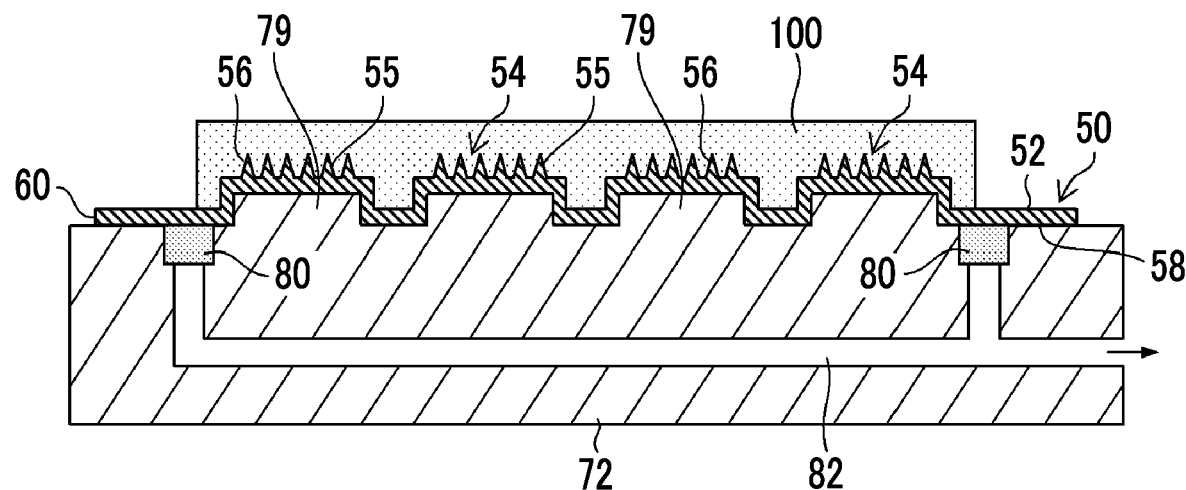
FIG. 11 is a process diagram illustrating the production method of a mold.

As illustrated in FIG. 11, the first mold 72 is separated from the second mold 74 and is moved to a stage for releasing the mold 100 from the electroform 50. In the present embodiment, since the second mold 74 having the depression 84 is separated from the mold 100, the mold 100 excluding the surface being in contact with the electroform 50 fixed to the first mold 72 is exposed. Therefore, in a case where the mold 100 is released from the electroform 50, it is possible to easily release the mold 100 using the exposed surface of the mold 100.

Figure 12:
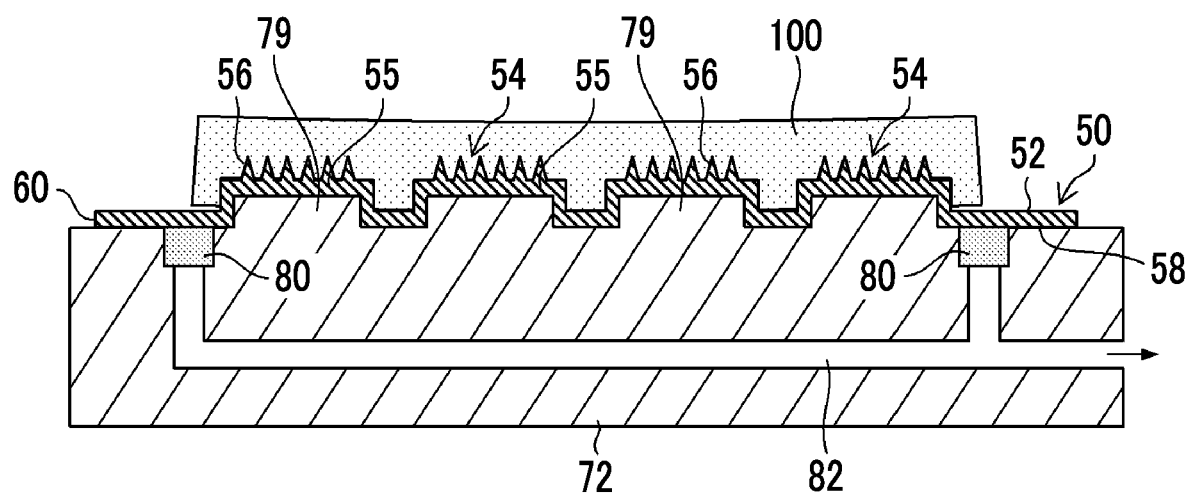
FIG. 12 is a process diagram illustrating the production method of a mold.

As illustrated in FIG. 12, the peripheral portion of the mold 100 is first separated from the electroform 50. The peripheral portion of the mold 100 may include at least two opposing sides in a case where the mold 100 is viewed in a plan view, and may include all of the four sides. The peripheral portion means a region from the outer periphery of the mold 100 to the recessed pattern 102.

As illustrated in FIG. 13, the peripheral portion of the mold 100 is gradually separated from the electroform 50. In a case where the mold 100 is made of a silicone resin, since the mold 100 has elasticity, the mold 100 enters a stretched state (elastically deforms) as the peripheral portion of the mold 100 is gradually separated. As the peripheral portion of the mold 100 is further separated from the electroform 50, the elastically deformed mold 100 tries to return to its original shape, so that the mold 100 contracts. By using the contraction force of the mold 100, the mold 100 is released from the electroform 50. By using the contraction force of the mold 100 as the releasing force, no excessive force is applied between the mold 100 and the protruding patterns 54 of the electroform 50, so that it is possible to suppress failure in releasing.

As illustrated in FIG. 14, finally, the mold 100 and the protruding patterns 54 of the electroform 50 are completely released from each other, and the mold 100 having the recessed patterns 102 is produced (releasing step). The recessed pattern 102 is a state in which a plurality of recesses 104 are arranged in a recessed pedestal pattern 105 in an array.

As a method of separating the peripheral portion of the mold 100 from the electroform 50, there is a method of suctioning the peripheral portion of the mold 100 in the exposed surface opposite to the surface on which the recessed patterns 102 are formed with suctioning means and separating the suctioning means from the electroform 50 while suctioning the peripheral portion.

In a case where the mold 100 is repeatedly produced from the electroform 50, the protruding patterns 54 are gradually damaged, and after use about 1000 to 10,000 times, it is necessary to replace the electroform 50 with a new electroform 50. In the present embodiment, by stopping the driving of the vacuum pump (not illustrated) and reducing the adsorption force of the adsorption plate 80, the electroform 50 can be replaced within a short period of time.

In the present embodiment, since the end portion 62 is not processed, the electroform 50 which is circular in a plan view is used in injection molding.

Figure 16:
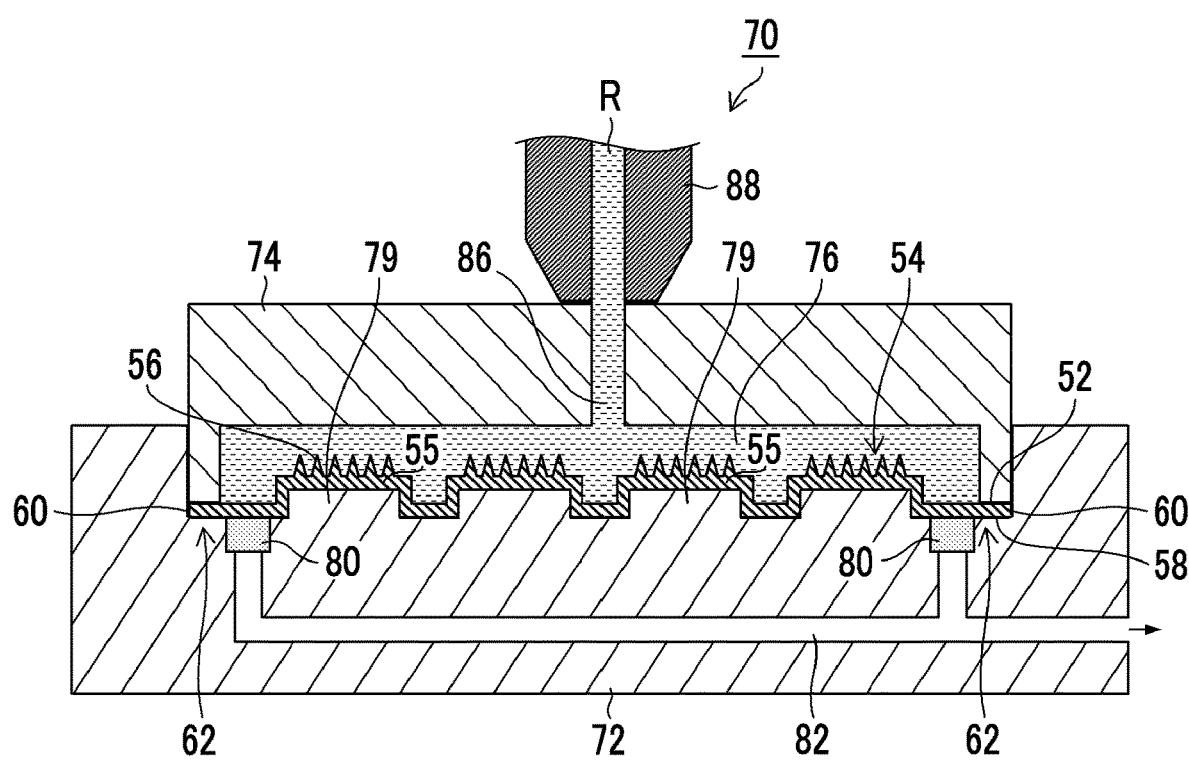
FIG. 16 is a process diagram illustrating the production method of another mold.

FIGS. 15 and 16 are process diagrams illustrating a production method of a mold using a mold 70 having another shape. As illustrated in FIG. 15, a depression 90 is formed in the first mold 72 of the mold 70. The electroform 50 is installed on the bottom surface of the depression 90, and is vacuum-adsorbed by the first mold 72 via the adsorption plate 80.

As illustrated in FIG. 16, in order to form the cavity 76, the first mold 72 and the second mold 74 are clamped. The electroform 50 installed in the depression 90 of the first mold 72 is clamped by the first mold 72 and the second mold 74. The inner wall of the second mold 74 is located inward of the outer edge 60 of the electroform 50 and outward of the adsorption plate 80. In addition, in the present embodiment, the end portion 62 of the electroform 50 is also clamped by the first mold 72 and the second mold 74.

As illustrated in FIG. 16, the resin R is supplied from the injection molding machine 88 to the cavity 76 via the gate 86. The resin R fills the cavity 76 while passing through between the protruding patterns 54 of the electroform 50.

<Problems in Case of Providing No Pedestal Support Portion>

The electroform 50, which is the insert mold according to the present embodiment, has a thickness of 150 μm. As described above, in the clamping step, the electroform 50 is clamped by the first mold 72 and the second mold 74. Even in a case where the end portion 62 of the electroform 50 has a warp and there is a distribution around the clamped portion, since the electroform 50 has a small thickness, the warp can be corrected by a clamping pressure of several tens of tons. Accordingly, no gap is formed in the clamped portion, and the injected resin does not leak. In addition, the warp of the electroform 50 inside the cavity can also be corrected by the resin pressure during injection so as to follow the first mold 72.

However, since the thickness of the electroform 50 is small, in a case where the pedestal support portion 79 is not provided on the first mold 72, there are problems that the protruding pedestal shape is buckled or broken by the injection pressure of the resin, and thus a desired recessed pedestal pattern 105 cannot be obtained in the formed mold 100.

Figure 17:
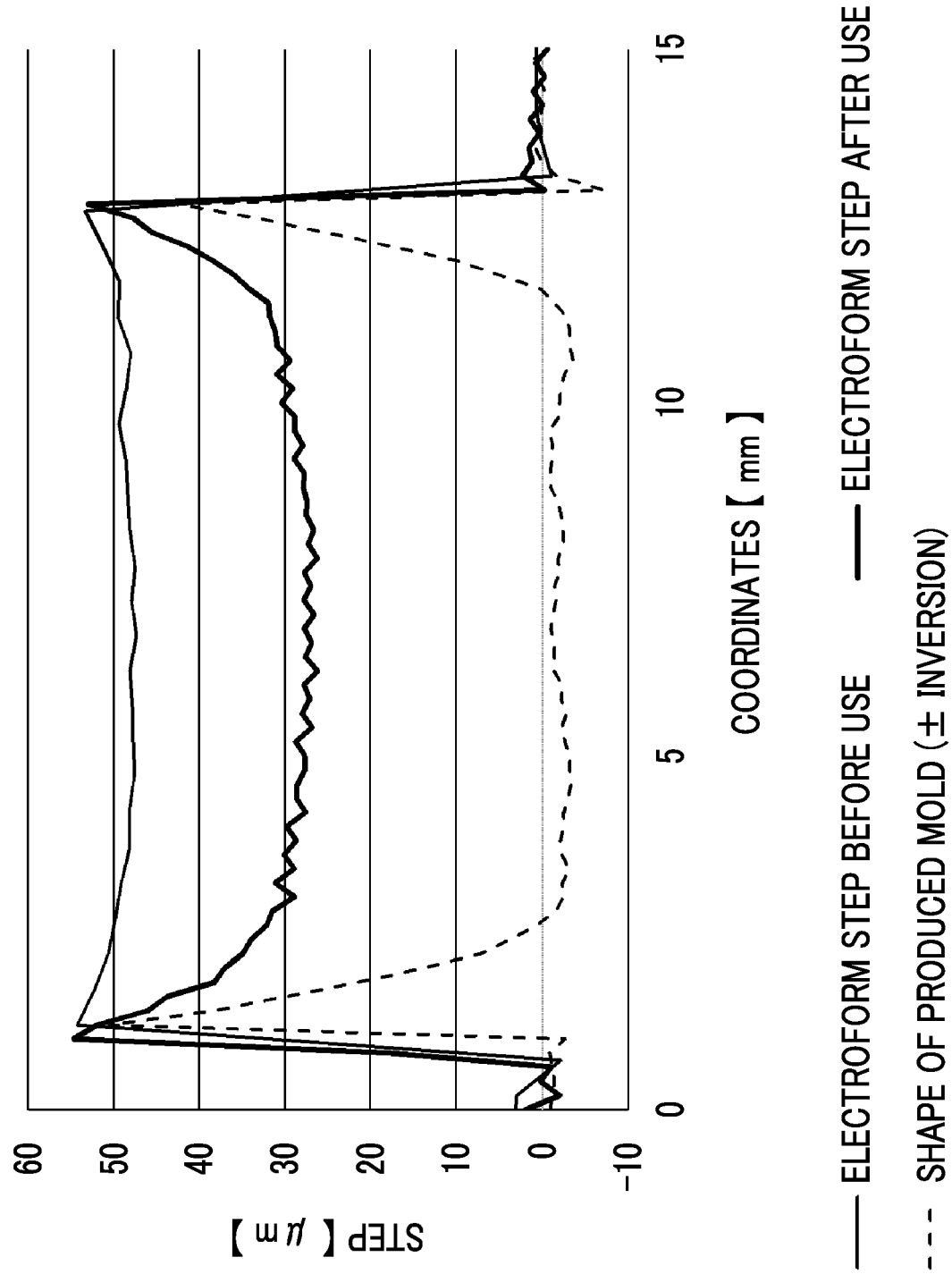
FIG. 17 is a diagram showing cross-sectional shapes of an insert mold and a mold.

FIG. 17 is a diagram showing cross-sectional shapes of the protruding pedestal shape of an insert mold before and after injection molding, and the recessed pedestal pattern shape of a mold produced without disposing a pedestal support portion on the rear surface of the protruding pedestal shape. In FIG. 17, the horizontal axis represents measurement position coordinates, and the vertical axis represents the height of the protruding pedestal shape and the depth (±inversion) of the recessed pedestal pattern shape. In FIG. 17, the protruding pedestal shape before injection molding is indicated by thin solid line, the protruding pedestal shape after injection molding is indicated by thick solid line, and the recessed pedestal pattern shape (±inversion) of the mold is indicated by broken line.

The protruding pedestal shape of the insert mold before injection molding is a portion of 1 mm to 13 mm in the measurement position coordinates shown in FIG. 17. As shown in FIG. 17, the protruding pedestal shape has a diameter of about 12 mm and a height of about 50 ium.

The recessed pedestal pattern shape of the produced mold is a portion of 1 mm to 13 mm in the measurement position coordinates shown in FIG. 17. As shown in FIG. 17, a portion of 3 to 11 mm in the measurement position coordinates has a height of about 0 μm. This is because the insert mold is pressed against the first mold surface by the injection pressure, and the protruding pedestal shape of the insert mold is buckled.

The protruding pedestal shape of the insert mold after injection molding is a portion of 1 mm to 13 mm in the measurement position coordinates shown in FIG. 17. As shown in FIG. 17, the protruding pedestal shape after injection molding in the portion of 3 to 11 mm in the measurement position coordinates has a height of about 30 μm. This is because the portion is plastically deformed by the injection pressure.

In order to avoid the occurrence of such buckling, it is conceivable to produce an insert mold having a large thickness. For example, in the case of an electroform, the plating time may be lengthened to increase the thickness.

However, if the entire insert mold is increased in thickness, the warp cannot be corrected in the clamping step, and a gap is generated in the clamped portion. There is a problem that the resin leaks in the clamped portion during the injection step even if the gap is about 10 μm. If the resin leaks, cleaning will be necessary for each injection molding, and the number of manual operations will increase, leading to an increase in costs such as labor costs and an increase in costs due to a reduction in the tact time of the apparatus.

In addition, a thickness distribution occurs in the mold along the shape of the warp of the insert mold. Accordingly, there is a problem that there is a difference in thickness between in-plane patches. If the thickness is different for each patch, focus adjustment is required for each patch during inspection. In addition, there is a possibility that the needle-like protrusions of the insert mold may collide with the second mold and be damaged.

In order to prevent the buckling of the protruding pedestal shape without increasing the thickness of the insert mold, it is considered that no space is provided on the rear surface of the protruding pedestal shape of the insert mold. In the case of an electroform, the thickness for electroforming may be increased and the electroform may be processed by grinding or the like.

However, increasing the thickness for the electroforming increases the electroforming time. If the height of the protruding pedestal shape is required to be about 500 μm, the thickness of the electroform is required to be about 750 μm, resulting in an increase in costs for the electroforming treatment.

In addition, if the insert mold has a thickness distribution, a gap is generated in the clamped portion during clamping. In order to prevent this, high processing accuracy is required, resulting in an increase in costs.

In view of such circumstances, in the present embodiment, the pedestal support portion 79 is disposed at the position of the first surface 52 of the first mold 72 corresponding to the recess 57 on the rear surface side of the first protrusion 55 of the electroform 50. By disposing the pedestal support portion 79, it is possible to prevent the protruding pedestal shape from buckling.

<Optimization of Pedestal Support Portion>

Figure 18:
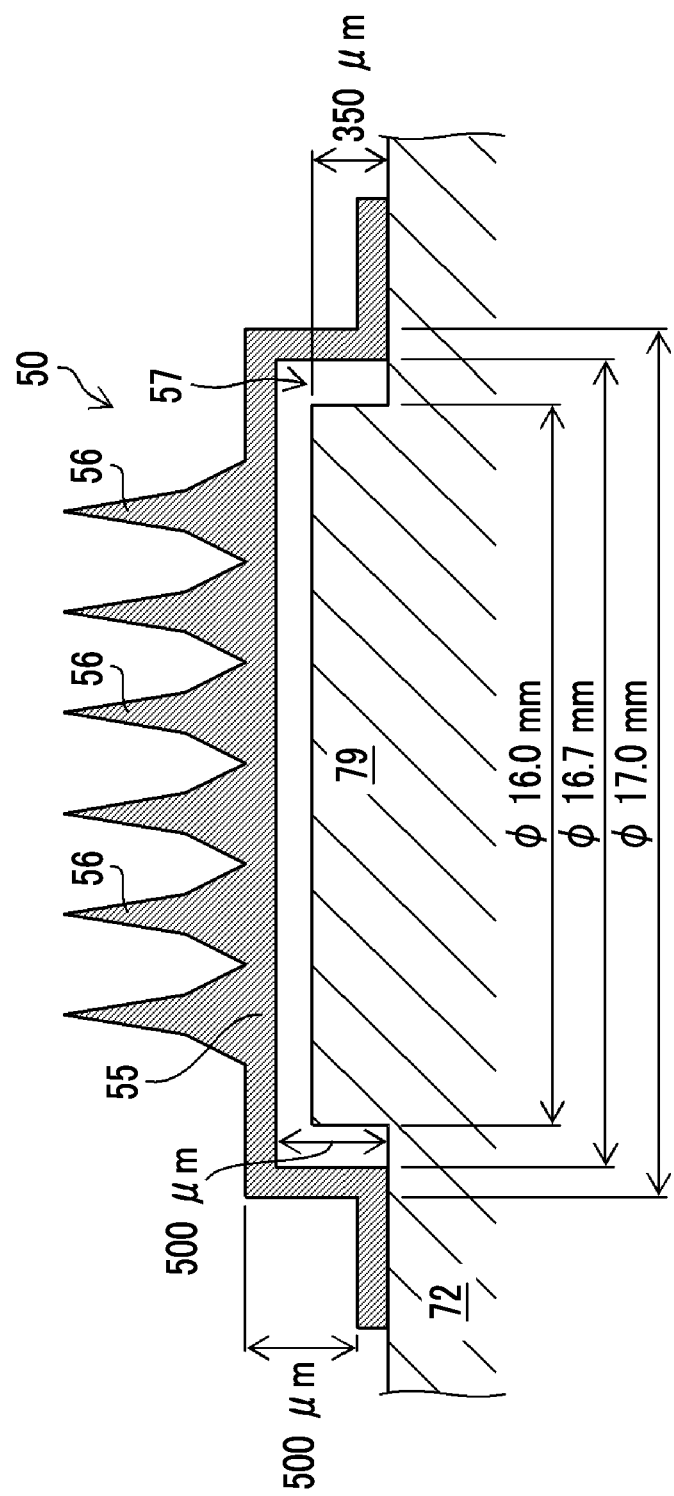
FIG. 18 is a cross-sectional view illustrating an example of a size relationship between a recess and a pedestal support portion.

FIG. 18 is a cross-sectional view illustrating an example of the size relationship between the recess 57 on the rear surface side of the first protrusion 55 of the electroform 50 and the pedestal support portion 79 of the first mold 72. In the example illustrated in FIG. 18, the first protrusion 55 has a height of 500 μm, and a diameter of 17.0 mm. The electroform 50 has a thickness of 150 μm, and the recess 57 has a depth of 500 μm, and an inner diameter of 16.7 mm.

The pedestal support portion 79 has a height of 350 μm and a diameter of 16.0 mm. The pedestal support portion 79 is set to have a small diameter in consideration of the difference in thermal expansion between the electroform 50 and the pedestal support portion 79.

Figure 19:
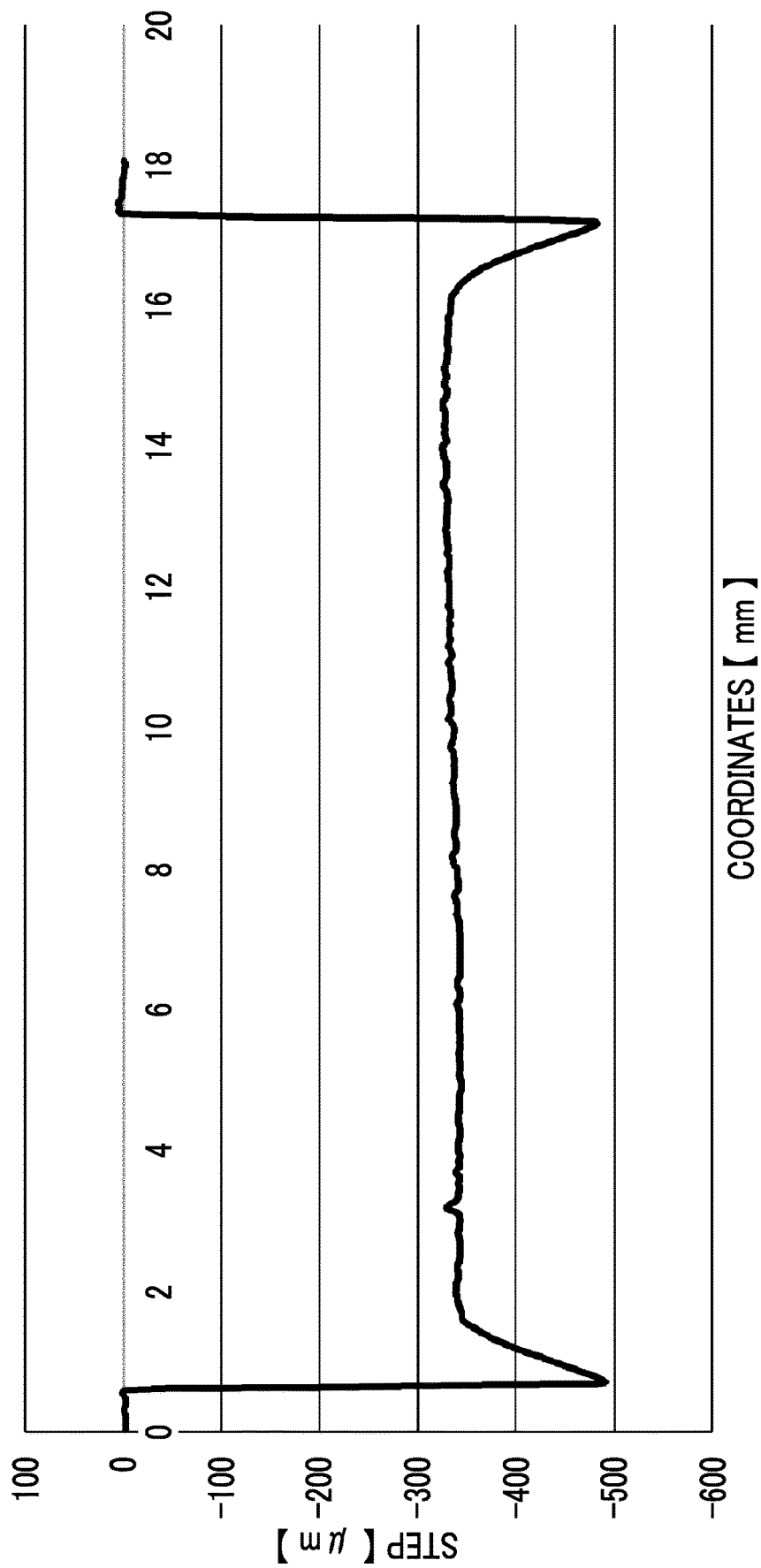
FIG. 19 is a graph showing a depth of a recessed pedestal pattern of the mold.

FIG. 19 is a diagram showing a cross-sectional shape of the recessed pedestal pattern shape of a mold produced using the electroform 50 and the first mold 72 illustrated in FIG. 18. The second protrusion 56 is ignored. In FIG. 19, the horizontal axis represents measurement position coordinates and the vertical axis represents the depth of the recessed pedestal pattern. The recessed pedestal pattern shape is a portion of 0.6 mm to 17.3 mm in the measurement position coordinates shown in FIG. 19. As illustrated in FIG. 19, the recessed pedestal pattern shape had a diameter of about 16.7 mm.

Furthermore, as shown in FIG. 19, the recessed pedestal pattern shape in the outer diameter (around 0.6 mm and around 17.3 mm in the measurement position coordinates) portion had a depth of about 490 μm. In addition, the depth of a portion of 1.9 mm to 16.0 mm in the measurement position coordinates was about 336 μm. By disposing the pedestal support portion 79 in this manner, a recessed pedestal pattern shape is formed in the mold.

Figure 20:
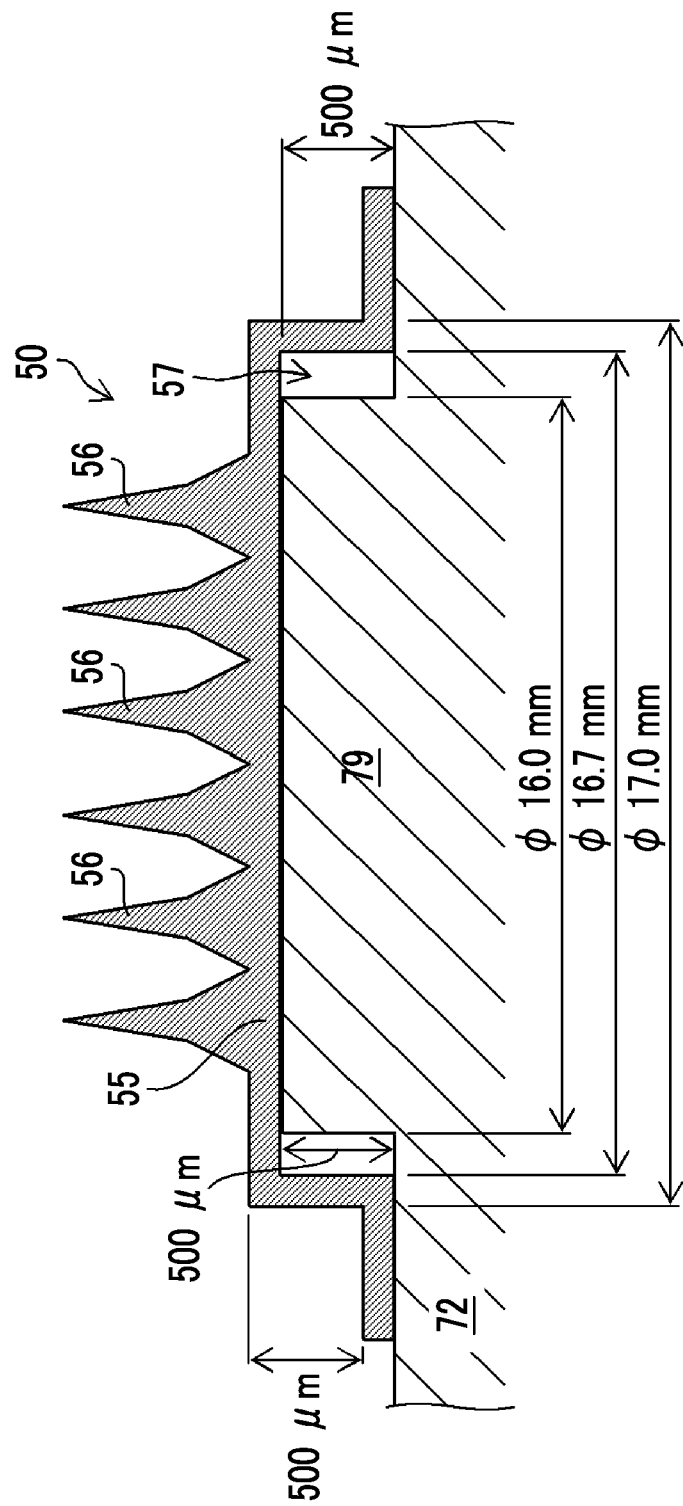
FIG. 20 is a cross-sectional view illustrating an example of a size relationship between the recess and the pedestal support portion.

FIG. 20 is a cross-sectional view illustrating an example of the size relationship between the recess 57 on the rear surface side of the first protrusion 55 of the electroform 50 and the pedestal support portion 79 of the first mold 72. In the example shown in FIG. 20, the sizes of the first protrusion 55 and the recess 57 of the electroform 50 are the same as those in the example illustrated in FIG. 18. The pedestal support portion 79 has a height of 500 μm, and a diameter of 16.0 mm. That is, the upper surface of the pedestal support portion 79 abuts the electroform 50.

Figure 21:
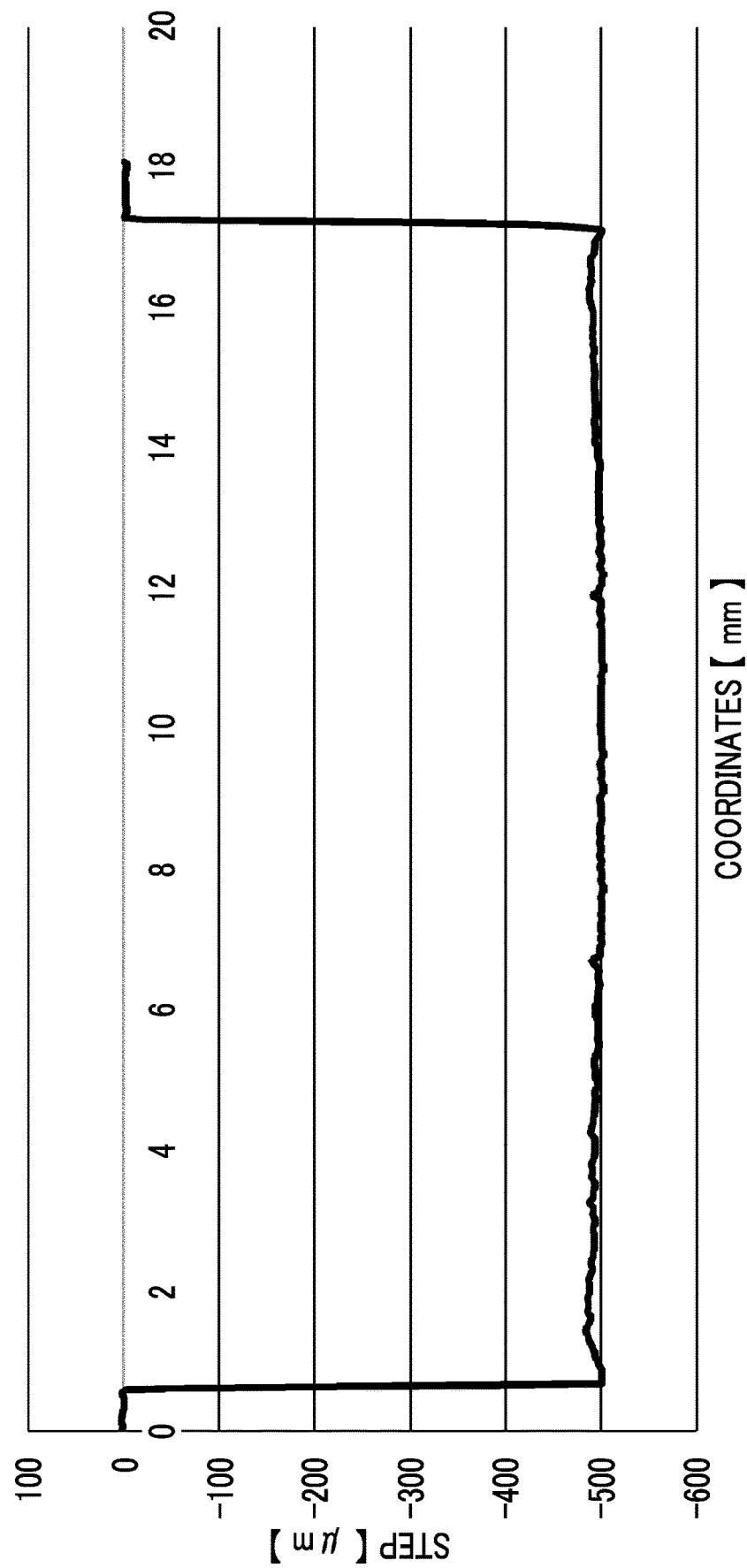
FIG. 21 is a graph showing the depth of the recessed pedestal pattern of the mold.

FIG. 21 is a diagram showing a cross-sectional shape of the recessed pedestal pattern shape of a mold produced using the electroform 50 and the first mold 72 illustrated in FIG. 20. The second protrusion 56 is ignored. In FIG. 21, the horizontal axis represents measurement position coordinates, and the vertical axis represents the depth of the recessed pedestal pattern. The recessed pedestal pattern shape is a portion of 0.6 mm to 17.3 mm in the measurement position coordinates shown in FIG. 21. As illustrated in FIG. 21, the recessed pedestal pattern shape had a diameter of about 16.7 mm.

Furthermore, as illustrated in FIG. 21, the recessed pedestal pattern shape in the portion of 0.6 mm to 17.3 mm in the measurement position coordinates had a depth of about 500 μm.

As described above, it could be seen that by causing the height of the pedestal support portion 79 to be equal to the depth of the recess 57, it is possible to form a recessed pedestal pattern shape having the depth of the recess 57 in the mold.

Second Embodiment

By providing the pedestal support portion 79 in the first mold 72, another aspect in which a recessed pedestal pattern is formed in a mold can be achieved.

Figure 22:
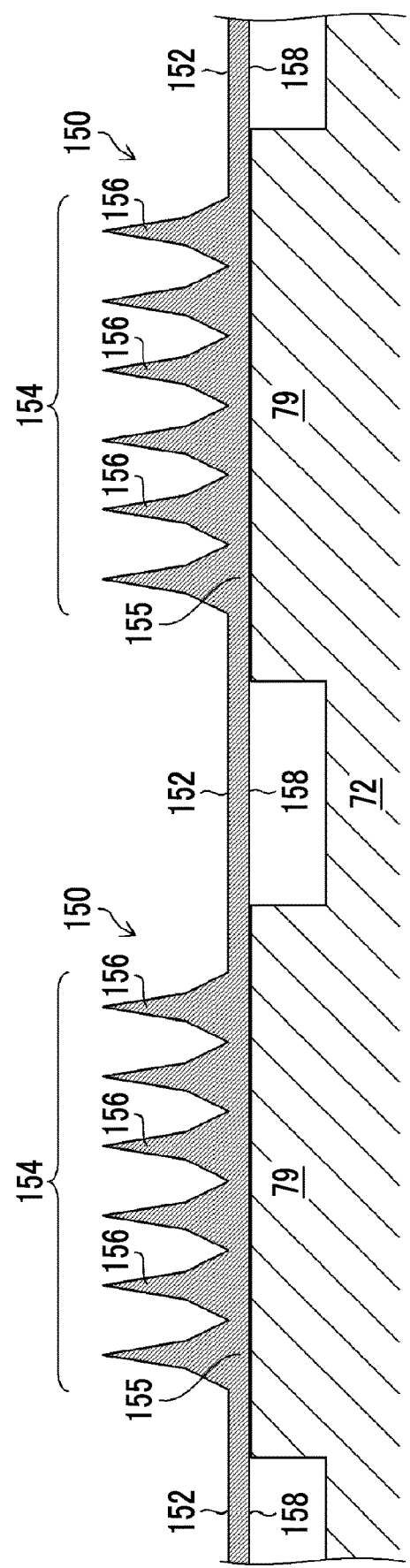
FIG. 22 is a diagram illustrating an electroform according to a second embodiment.

In a second embodiment, a thin metal or soft resin is used as the insert mold. Here, an electroform 150 is prepared as an insert mold. As illustrated in FIG. 22, the electroform 150 has a first surface 152 and a second surface 158, and protruding patterns 154 are provided on the first surface 152. The protruding pattern 154 is a state in which a plurality of second protrusions 156 (protruding needle pattern group) are arranged in an array. The electroform 150 does not have a protruding pedestal shape corresponding to the first protrusion 55 of the electroform 50 of the first embodiment at this point.

The protruding pattern 154 of the electroform 150 is held on the pedestal support portion 79 of the first mold 72 in an overlapping manner to form a cavity, so that the electroform 150 is clamped by the first mold 72 and the second mold 74 (clamping step).

Figure 23:
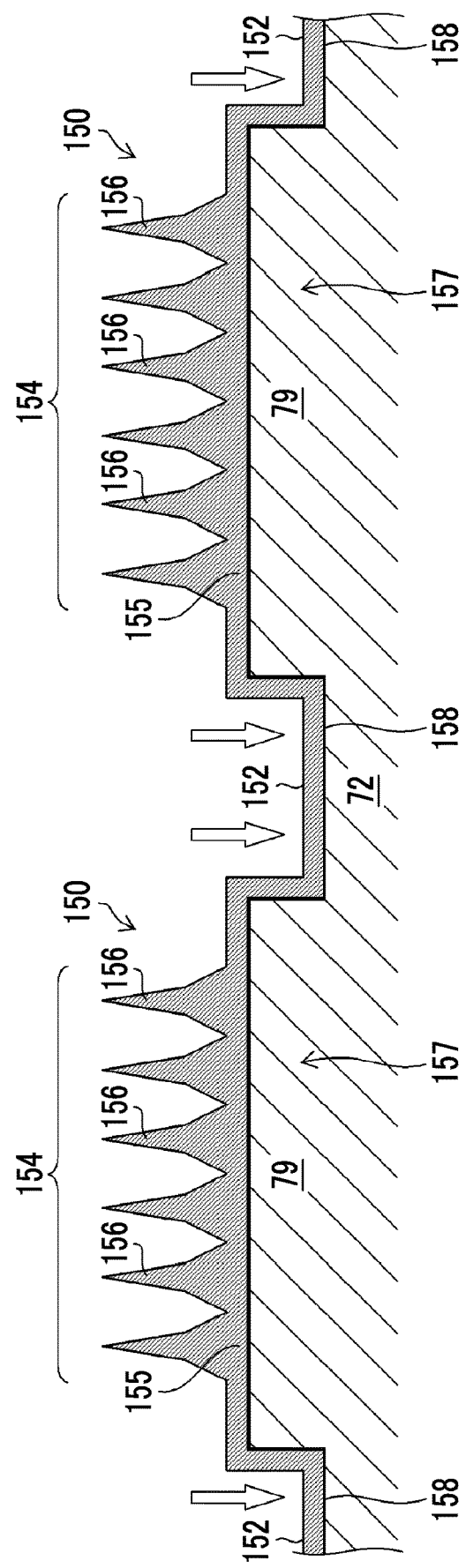
FIG. 23 is a diagram illustrating a modified electroform.

Subsequently, the cavity is filled with a resin (injection step). In the injection step, the electroform 150 is deformed following the pedestal support portion 79 to form a protruding pedestal shape having a recess on the rear surface of the electroform 150. That is, as illustrated in FIG. 23, the electroform 150 is deformed following the pedestal support portion 79 by the pressure of the injected resin. Accordingly, the protruding pattern 154 of the electroform 150 enters a state in which the plurality of second protrusions 156 (protruding needle pattern group) are arranged in an array on the first protrusion 155 (protruding pedestal shape). On the rear surface side of the first protrusion 155, a cylindrical recess 157 that follows the pedestal support portion 79 is provided.

That is, the depth of the recess 157 is equal to the height of the pedestal support portion 79. Therefore, a mold having the same shape as the mold 100 according to the first embodiment can be produced.

The first protrusion 155 of the electroform 150 remains formed even after the electroform 150 is detached by opening the first mold 72 and the second mold 74. That is, the recess 157 maintains a depth equal to the height of the pedestal support portion 79. Therefore, in a case where the electroform 150 is used again, as in the electroform 50, the pedestal support portion 79 of the first mold 72 may be fitted into the recess 157 of the electroform 150 such that the pedestal support portion 79 and the protruding pattern 154 are held in an overlapping manner. Accordingly, a mold having the same shape as the mold 100 according to the first embodiment can be produced.

As described above, according to the present embodiment, the recess 157 having a depth equal to the height of the pedestal support portion 79 can be formed by injection molding in the electroform 150 provided with the protruding pattern 154.

Third Embodiment

Figure 24:
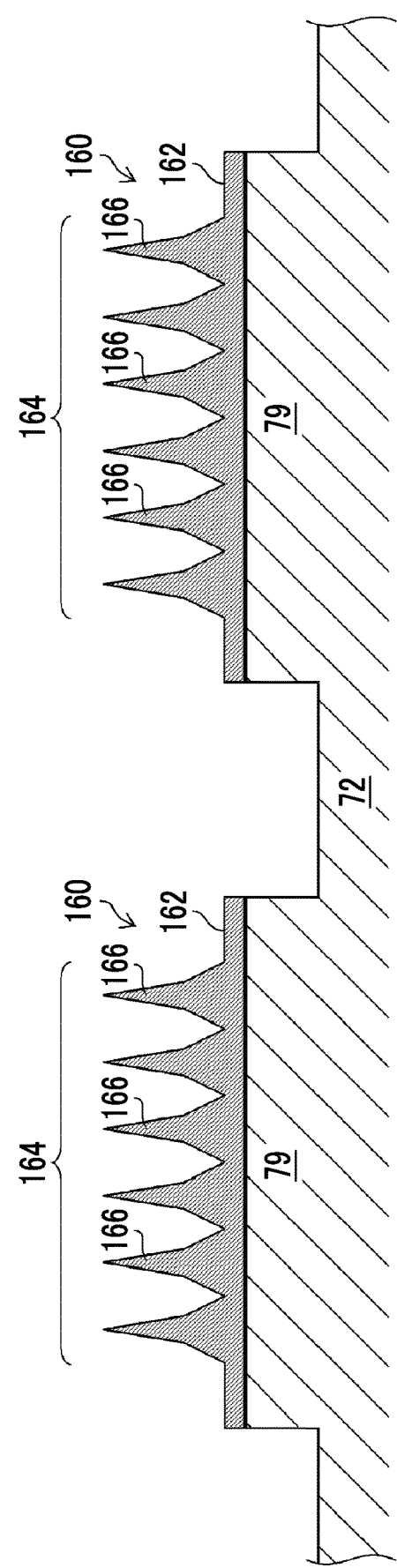
FIG. 24 is a diagram illustrating an electroform according to a third embodiment.

In a third embodiment, the material and the thickness of an insert mold are not limited. Here, an electroform 160 is prepared as an insert mold. As illustrated in FIG. 24, the electroform 160 has protruding patterns 164 on a first surface 162. The protruding pattern 164 is a state in which a plurality of protrusions 166 (protruding needle pattern group) are arranged in an array. The electroform 160 has a plurality of protrusions 166 corresponding to the plurality of second protrusions 56 of the electroform 50 of the first embodiment, and does not have portions corresponding to the flat portion 53 and the first protrusion 55. Accordingly, the electroform 160 has the same size as the pedestal support portion 79 of the first mold 72 or is smaller than the pedestal support portion 79 in a plan view.

The electroform 160 is held on the pedestal support portion 79 of the first mold 72 in an overlapping manner. Here, the electroform 160 is formed of a ferromagnetic material such as nickel and is held by the first mold 72 by the magnetic force of a magnet (not illustrated) provided in the first mold 72. In this state, clamping is performed by the first mold 72 and the second mold 74 (clamping step).

Subsequently, the cavity is filled with a resin (injection step). Accordingly, a mold having the same shape as the mold 100 according to the first embodiment can be produced.

According to the present embodiment, by using the small electroform 160 provided with only the protruding pattern 164 corresponding to the pedestal support portion 79, a mold having a recessed pedestal pattern can be produced without causing buckling. Furthermore, by using a plurality of electroforms 160, a mold having a plurality of recessed pedestal patterns can be produced.

<Manufacturing Method of Pattern Sheet>

Next, a method of manufacturing a pattern sheet using the mold 100 produced in the above-described production method will be described. FIGS. 25 to 28 are process diagrams for manufacturing a pattern sheet 110.

[Polymer Solution Supplying Step]

Figure 25:
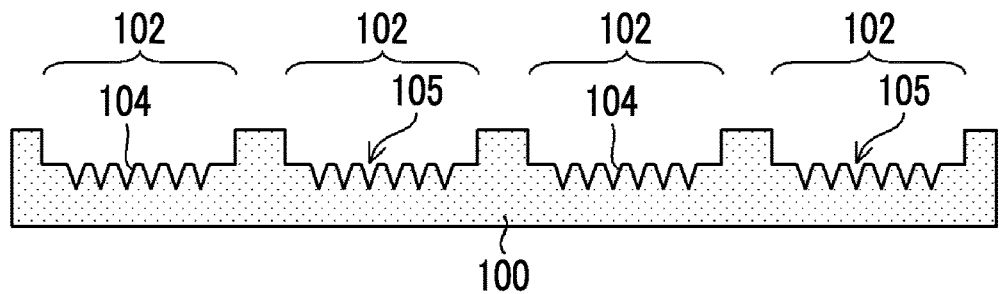
FIG. 25 is a process diagram illustrating a manufacturing method of a pattern sheet.

FIG. 25 illustrates a state in which the mold 100 is prepared. The mold 100 is manufactured by the production method of the mold described above. The mold 100 illustrated in FIG. 25 has a plurality of the recessed patterns 102. The recessed pattern 102 is a state in which a plurality of recesses 104 are arranged in an array.

Figure 26:
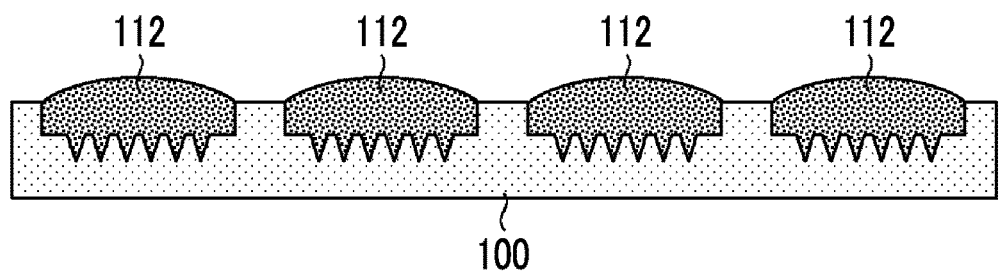
FIG. 26 is a process diagram illustrating the manufacturing method of a pattern sheet.

FIG. 26 is a diagram illustrating a supplying step of supplying a polymer solution 112 to the recessed patterns 102 of the mold 100.

As the material of the polymer solution 112 forming the pattern sheet 110, it is preferable to use a water-soluble material. As a material of a resin polymer of the polymer solution 112 used to manufacture the pattern sheet 110, it is preferable to use a biocompatible resin. As such resins, sugars such as glucose, maltose, pullulan, sodium chondroitin sulfate, sodium hyaluronate, and hydroxyethyl starch, proteins such as gelatin, and biodegradable polymers such as polylactic acid and a lactic acid-glycolic acid copolymer are preferably used. In a case where the pattern sheet 110 is released from the mold 100, the pattern sheet 110 can be released using a base material (not illustrated), so that such resins can be suitably used. Although a concentration varies depending on the material, it is preferable that the concentration is set so that the resin polymer is contained at 10 to 50 mass % in the polymer solution 112 which does not contain a drug. A solvent used in the polymer solution 112 may be warm water or may be volatile, and alcohol such as ethanol or the like may be used. In addition, it is possible to dissolve the drug, which is supplied into the body according to the application, in the polymer solution 112. The polymer concentration of the polymer solution 112 containing the drug (the concentration of the polymer excluding the drug in a case where the drug itself is a polymer) is preferably 0 to 30 mass %.

As a method of preparing the polymer solution 112, in a case where a water-soluble polymer (such as gelatin) is used, a water-soluble powder may be dissolved in water and the drug may be added after the dissolution. Otherwise, a powder of a water-soluble polymer may be dissolved in a liquid in which the drug is dissolved. In a case where it is difficult to dissolve the polymer in water, heating may be performed for dissolution. The temperature can be appropriately selected depending on the kind of the polymer material, and it is preferable that heating is performed at a temperature of about 20° C. to 40° C. For the solution containing the drug, the viscosity of the polymer solution 112 is preferably 200 mPa·s or less, and more preferably 50 mPa·s or less. For a solution which does not contain a drug, the viscosity is preferably 2000 mPa·s or less, and more preferably 500 mPa·s or less. By appropriately adjusting the viscosity of the polymer solution 112, the polymer solution 112 can be easily injected into the recessed patterns 102 of the mold 100. For example, the viscosity of the polymer solution 112 can be measured with a capillary viscometer, a falling ball viscometer, a rotational viscometer, or a vibrational viscometer.

The drug to be contained in the polymer solution 112 is not limited as long as the drug has a function of a drug. In particular, the drug is preferably selected from peptides, proteins, nucleic acids, polysaccharides, vaccines, pharmaceutical compounds that belong to a water-soluble low molecular weight compound, or cosmetic ingredients.

Examples of a method of injecting the polymer solution 112 into the mold 100 include application using a spin coater.

It is preferable to form a through-hole at the tip of the recess of the recessed pattern 102 of the mold 100. The air in the recess of the recessed pattern 102 can escape from the through-hole. Therefore, the polymer solution 112 can easily enter the recess of the mold 100. In addition, this step is preferably performed in a decompressed state.

[Drying Step]

Figure 27:
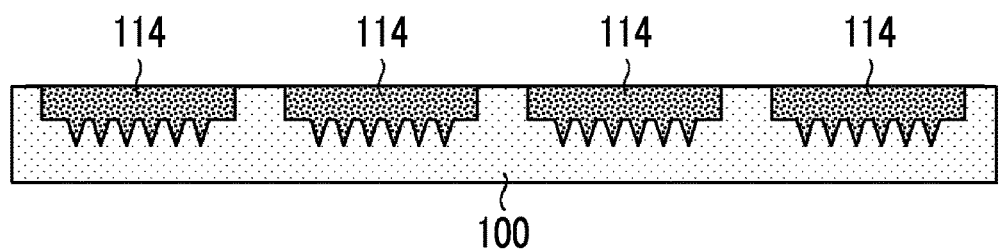
FIG. 27 is a process diagram illustrating the manufacturing method of a pattern sheet.

FIG. 27 is a diagram illustrating a drying step of drying the polymer solution 112 to form a polymer sheet 114. For example, the polymer solution 112 supplied to the mold 100 can be dried by blowing air thereto. The polymer sheet 114 means a state after a desired drying treatment is applied to the polymer solution 112. The moisture content of the polymer sheet 114 and the like are appropriately set. In addition, as the moisture content of the polymer becomes too low due to the drying, it becomes difficult to peel off the polymer sheet 114. Therefore, it is preferable to keep the moisture content in a state of maintaining elasticity.

[Polymer Sheet Releasing Step]

Figure 28:
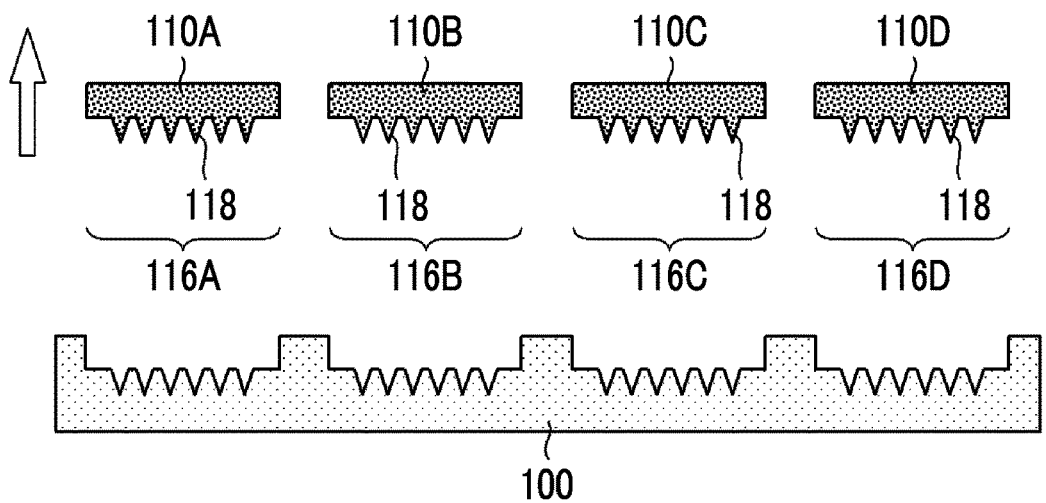
FIG. 28 is a process diagram illustrating the manufacturing method of a pattern sheet.
Figure 29:
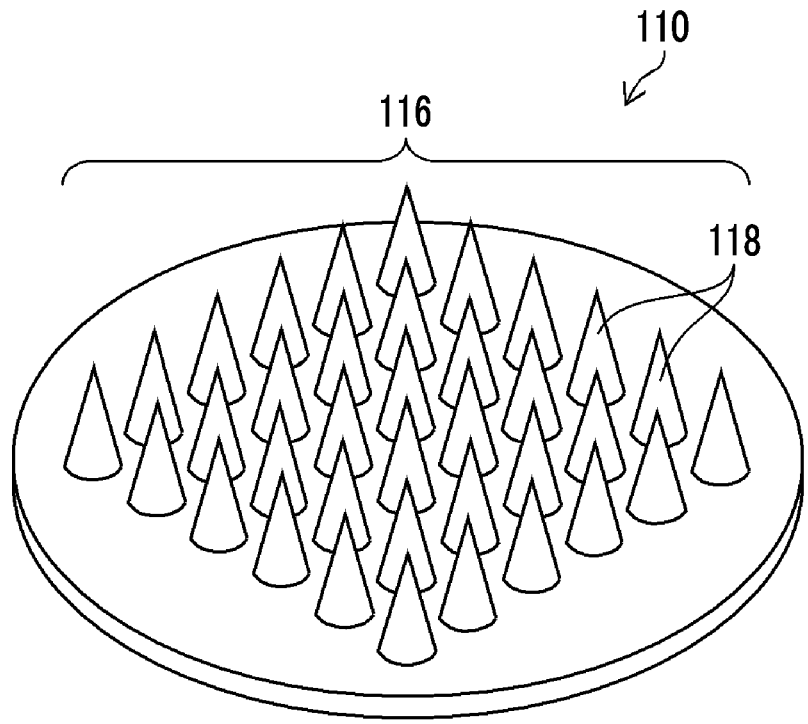
FIG. 29 is a perspective view of a pattern sheet.

FIG. 28 is a diagram illustrating a polymer sheet releasing step of releasing the polymer sheet 114 from the mold 100 to form individual pattern sheets 110A, 110B, 110C, and 110D. The pattern sheets 110A, 110B, 110C, and 110D respectively have protruding patterns 116A, 116B, 116C, and 116D on one surface. In the following, the pattern sheets 110A, 110B, 110C, and 110D are referred to as a pattern sheet 110 as a representative, and the protruding patterns 116A, 116B, 116C, and 116D are referred to as a protruding pattern 116 as a representative. FIG. 29 is a perspective view of the pattern sheet 110.

In the present embodiment, the case where the polymer sheet 114 is formed by filling the recessed pattern 102 of the mold 100 with the polymer solution 112 and drying the resultant has been described above, but the formation of the polymer sheet 114 is not limited thereto.

For example, a polymer sheet 114 having a two-layer structure can be formed by filling the recessed pattern 102 of the mold 100 with the polymer solution 112 containing the drug, drying the resultant, thereafter filling the recessed pattern 102 of the mold 100 with the polymer solution 112 containing no drug, and drying the resultant.

In addition, there may be cases where the mold 100 is used only once and is preferably disposable. In a case where the pattern sheet 110 is used as a medicine, the pattern sheet 110 is preferably disposable in consideration of the safety of the manufactured pattern sheet 110 for the living body. By making the pattern sheet 110 disposable, there is no need to clean the mold 100, so that the cost of the cleaning can be reduced. In particular, in a case where the pattern sheet 110 is used as a medicine, high cleaning performance is required, so that the cleaning cost is high.

The protruding pattern 116 of the manufactured pattern sheet 110 refers to a state in which a plurality of a predetermined number of protrusions 118 are arranged in an array at predetermined positions. The protrusion 118 means a shape tapered toward the tip and includes a cone shape and a multistage cone shape. The multistage cone shape means a cone shape having sides at different angles from the bottom to the tip.

The height of the protrusion 118 is in a range of 0.2 mm or more and 2 mm or less, and preferably 0.3 mm or more and 1.5 mm or less.

The manufactured pattern sheet 110 having the protruding pattern 116 is a duplicate of the electroform 50 having the protruding pattern 54. By setting the shape and arrangement of the protruding pattern 54 of the electroform 50 to a desired shape, the protruding pattern 116 of the manufactured pattern sheet 110 can be formed into a desired shape.

<Production Method of Electroform Having Protruding Pattern>

Figure 30:
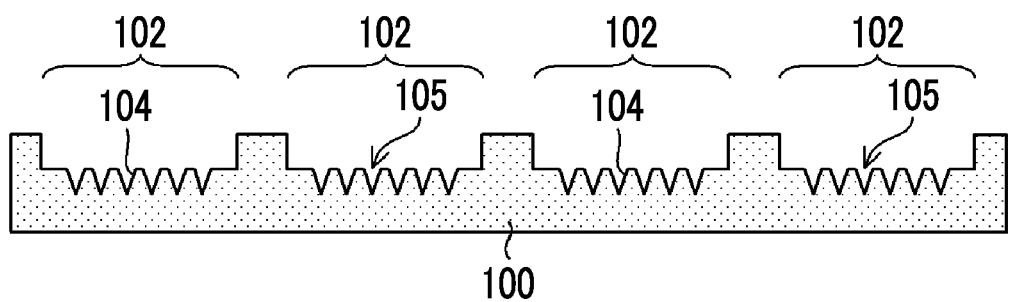
FIG. 30 is a process drawing illustrating a procedure of a production method of an electroform using a mold.
Figure 31:
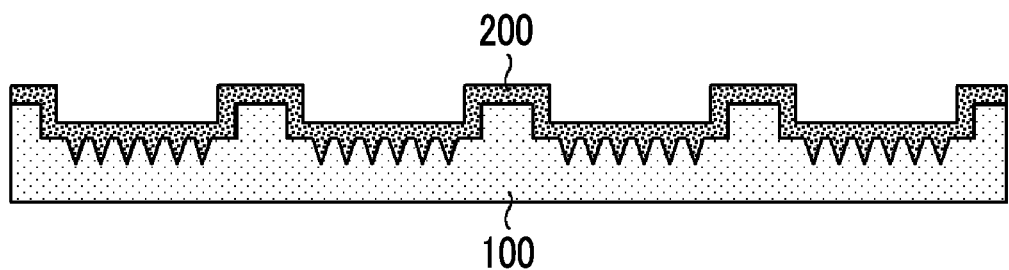
FIG. 31 is a process drawing illustrating the procedure of the production method of an electroform using a mold.
Figure 32:
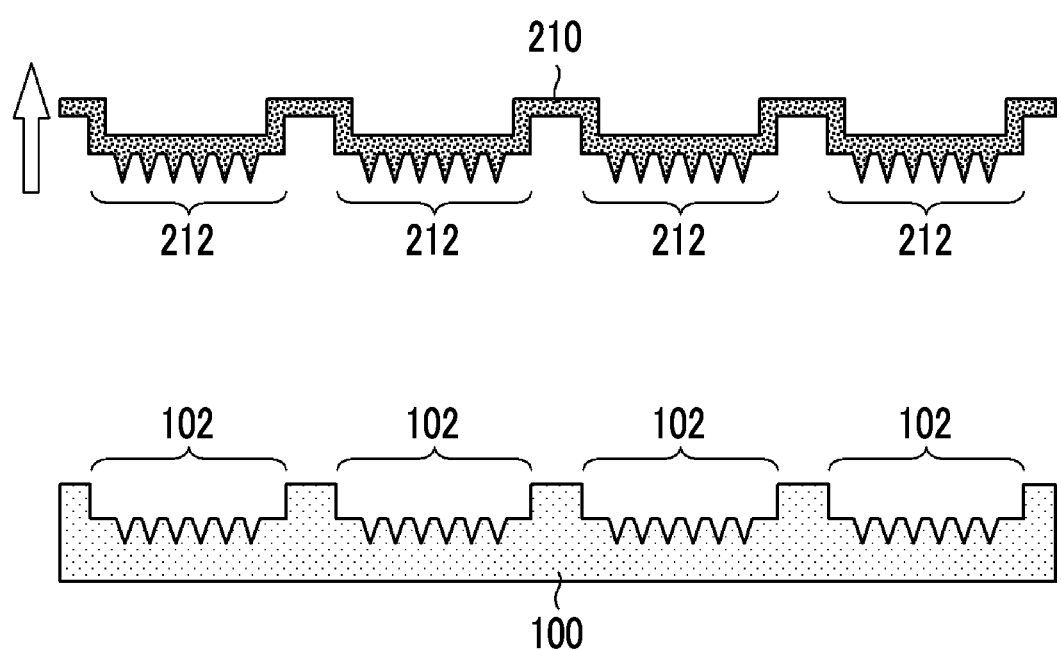
FIG. 32 is a process drawing illustrating the procedure of the production method of an electroform using a mold.

Next, a method for producing an electroform using the mold 100 will be described. FIGS. 30 to 32 are process diagrams illustrating the procedure of the production method of an electroform using the mold 100.

FIG. 30 illustrates a state where the mold 100 (an example of a first mold) is prepared. The mold 100 is manufactured by the production method of the mold described above. The mold 100 has a plurality of the recessed patterns 102. The recessed pattern 102 is a state in which a plurality of recesses 104 are arranged in an array.

FIG. 31 is a process diagram illustrating an electroforming step of burying the recessed pattern 102 of the mold 100 with a metal by an electroforming treatment. In the electroforming step, first, the mold 100 is subjected to a conduction treatment. A metal (for example, nickel) is sputtered on the mold 100 such that the metal adheres onto the surface of the mold 100 and the recessed pattern 102.

Next, the mold 100 that has been subjected to the conduction treatment is held on a cathode. Metal pellets are held in a metal case and used as an anode. The cathode holding the mold 100 and the anode holding the metal pellets are immersed in an electroforming liquid and energized. The recessed pattern 102 of the mold 100 is buried with the metal by the electroforming treatment method, whereby a metal body 200 is formed.

FIG. 32 is a process diagram illustrating a peeling step of peeling the metal body 200 from the mold 100. As illustrated in FIG. 32, the metal body 200 is peeled from the mold 100, and an electroform 210 having protruding patterns 212 is produced. Peeling means that the metal body 200 and the mold 100 are separated from each other. The protruding pattern 212 has an inverted shape of the recessed pattern 102 of the mold 100. Here, the electroform 210 is basically the same as the metal body 200 peeled from the mold 100.

By using the electroform 210 thus produced as an insert mold instead of the electroform 50, a mold (an example of a second mold) can be produced by injection molding.

<Others>

The technical scope of the present invention is not limited to the scope described in the above embodiments. The configurations and the like in the embodiments can be appropriately combined between the embodiments without departing from the gist of the present invention.

EXPLANATION OF REFERENCES

10: master model
12: first surface

14: recessed pattern
15: first recess
16: second recess
18: second surface
20: cathode
22: shaft
24: cathode plate
26: conductive ring
30: electroforming apparatus
32: electroforming liquid
32A: electroforming liquid
34: electroforming tank
36: drain tank
38: Ni pellet
40: titanium case
42: drain pipe
44: supply pipe
50: electroform
52: first surface
53: flat portion
54: protruding pattern
55: first protrusion
56: second protrusion
57: recess
58: second surface
60: outer edge
62: end portion
70: mold
72: first mold
74: second mold
76: cavity
78: flat surface
79: pedestal support portion
80: adsorption plate
82: suction pipe
84: depression
86: gate
88: injection molding machine
90: depression
100: mold
102: recessed pattern
104: recess
105: recessed pedestal pattern
110: pattern sheet
112: polymer solution
114: polymer sheet
116: protruding pattern
118: protrusion
150: electroform
152: first surface
154: protruding pattern
155: first protrusion
156: second protrusion
157: recess
158: second surface
160: electroform
162: first surface
164: protruding pattern
166: protrusion
200: metal body
210: electroform
212: protruding pattern

What is claimed is:

1. A production method of a mold having a recessed pedestal pattern, comprising:
a step of preparing an insert mold having a protruding needle pattern group;
a step of preparing a mold having a first mold provided with a protruding pedestal shape and a second mold;
a holding step of holding the protruding pedestal shape of the first mold and the protruding needle pattern group of the insert mold in an overlapping manner;
a clamping step of performing clamping with the first mold and the second mold to form a cavity; and
an injection step of filling the cavity with a resin,
wherein in the injection step, the insert mold is deformed following the protruding pedestal shape of the first mold to form a protruding pedestal shape having a recess on a rear surface of the insert mold.

2. The production method of a mold having a recessed pedestal pattern according to claim 1,
wherein the insert mold has the protruding needle pattern group on a front surface of a protruding pedestal shape having a recess on a rear surface, and
in the holding step, the protruding pedestal shape of the first mold and the recess of the insert mold are held in an overlapping manner.

3. The production method of a mold having a recessed pedestal pattern according to claim 1,
wherein the insert mold has the same size as the protruding pedestal shape in a plan view or is smaller than the protruding pedestal shape.

4. The production method of a mold having a recessed pedestal pattern according to claim 1,
wherein the resin is any one of a thermosetting resin and a silicone resin.

5. The production method of a mold having a recessed pedestal pattern according to claim 1, further comprising:
after the injection step, a curing step of heating the resin in the cavity to cure the resin; and
after the curing step, a releasing step of opening the first mold and the second mold and releasing the cured resin from the insert mold.

6. The production method of a mold having a recessed pedestal pattern according to claim 1,
wherein the insert mold is made of any one of a plastic resin and a metal.

7. The production method of a mold having a recessed pedestal pattern according to claim 1,
wherein the insert mold is an electroform and is circular in a plan view.

8. The production method of a mold having a recessed pedestal pattern according to claim 1,
wherein, in the clamping step, the insert mold is clamped by the first mold and the second mold.

9. A production method of a mold having a recessed pedestal pattern, comprising:
a step of producing a first mold having a recessed pedestal pattern by the production method of a mold having a recessed pedestal pattern according to claim 1;
an electroforming step of forming a metal body on the recessed pedestal pattern of the first mold by an electroforming treatment;
a peeling step of peeling the metal body that is an electroform from the first mold; and
a step of producing a second mold by the production method of a mold having a recessed pedestal pattern according to claim 1, using the electroform as an insert mold.

10. A manufacturing method of a pattern sheet, comprising:
a step of producing a mold having a recessed pedestal pattern by the production method of a mold having a recessed pedestal pattern according to claim 1;

a supplying step of supplying a polymer solution to the recessed pedestal pattern of the mold;

a drying step of drying the polymer solution to form a polymer sheet; and a polymer sheet releasing step of releasing the polymer sheet from the mold.

11. The manufacturing method of a pattern sheet according to claim 10, wherein the polymer solution contains a water-soluble material.

\* \* \* \* \*